United States Patent
Dhanoa

(10) Patent No.: US 9,271,979 B2
(45) Date of Patent: Mar. 1, 2016

(54) DEUTERIUM-ENRICHED PYRIMIDINE COMPOUNDS AND DERIVATIVES

(76) Inventor: Daljit Singh Dhanoa, Del Mar, CA (US)

( * ) Notice: Subject to any disclaimer, the term of this patent is extended or adjusted under 35 U.S.C. 154(b) by 469 days.

(21) Appl. No.: 13/199,940

(22) Filed: Sep. 14, 2011

(65) Prior Publication Data
US 2012/0035191 A1 Feb. 9, 2012

Related U.S. Application Data

(63) Continuation-in-part of application No. 12/804,970, filed on Aug. 3, 2010.

(51) Int. Cl.
| | |
|---|---|
| A61K 31/519 | (2006.01) |
| A61P 9/12 | (2006.01) |
| A61P 25/22 | (2006.01) |
| A61P 25/24 | (2006.01) |
| A61P 35/00 | (2006.01) |
| C07D 495/04 | (2006.01) |
| C07B 59/00 | (2006.01) |
| C07D 513/04 | (2006.01) |

(52) U.S. Cl.
CPC ............ *A61K 31/519* (2013.01); *C07B 59/002* (2013.01); *C07D 495/04* (2013.01); *C07D 513/04* (2013.01)

(58) Field of Classification Search
CPC . C07D 495/04; A61K 31/519; C07B 2200/05
USPC .......................... 544/278; 514/260.1
See application file for complete search history.

(56) References Cited

PUBLICATIONS

Svenja, B. et al. "The 5-HT2B Receptor Plays a Key Regulatory Role in Both Neuroendrocrine Tumor Cell Proliferation and the Modulation of the Fibroblast Component of the Neoblastic Microenviroment"; Cancer, 116, pp. 2902-2912.*

* cited by examiner

Primary Examiner — Susanna Moore

(57) ABSTRACT

The present invention is concerned with deuterium-enriched pyrimidine compounds of formula 1, their derivatives and pharmaceutically acceptable salts and methods of use thereof

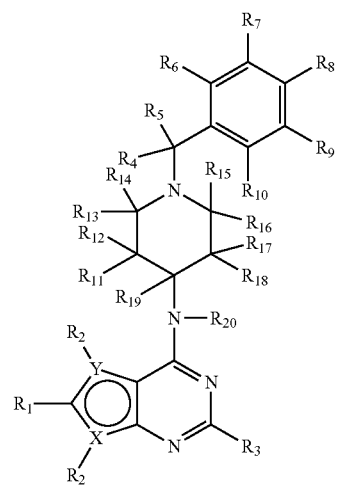

for the prevention and treatment of neuroendocrine neoplasia including metastasis and fibrosis, fibrotic processes associated with neuroendocrine cell dysregulation for example Crohn's disease, pulmonary arterial hypertension, pulmonary hypertension associated with chronic obstructive pulmonary disease (COPD), right ventricular hypertrophy, pulmonary vascular remodeling, asthma, cystic fibrosis, hypertension, ischemic stroke, angina pectoris, congestive heart failure, arrhythmia, arterial fibrillation, neurodenerative diseases, gastrointestinal disorders, stress disorders, obsessive compulsive disorders, demyelinating diseases, cerebral vascular disorders, bronchoconstriction, vasodilation, smooth muscle contraction, brain disorders, vascular disorders, neuropathological diseases and cardiovascular system regulation.

20 Claims, No Drawings

DEUTERIUM-ENRICHED PYRIMIDINE COMPOUNDS AND DERIVATIVES

RELATED U.S. APPLICATION DATA

Continuation-in-part (CIP) of U.S. patent application Ser. No. 12/804,970, filed on Aug. 3, 2010.

CROSS-REFERENCE TO RELATED APPLICATIONS

This application claims the benefit of priority under 35 U.S.C.119(e) to U.S. patent application publication number: Ser. No. 12/804,970, filed on Aug. 3, 2010, which is incorporated by reference in its entirety.

SUMMARY OF THE INVENTION

This invention is concerned with pyrimidine compounds and their derivatives of the formula I and pharmaceutically acceptable salts thereof,

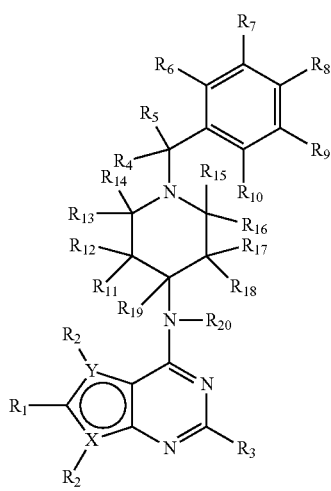

I wherein,
when X=S, Y is C or N; when Y is C, it is substituted with $R_2$;
when Y=S, X is C or N; when X is C, it is substituted with $R_2$;
$R_1$ is D (Deuterium), F, Cl;
$R_2$ is D, F, Cl;
$R_3$ is H, D;
$R_4$ and $R_5$ are D, H;
$R_6$, $R_7$, $R_8$, $R_9$ and $R_{10}$ are D, H, F, Cl, CN;
$R_{11}$, $R_{12}$, $R_{13}$, $R_{14}$, $R_{15}$, $R_{16}$, $R_{17}$, $R_{18}$, and $R_{19}$ are D, H;
$R_{20}$ is D, H;
and salts thereof.

BACKGROUND OF THE INVENTION

Neurotransmitter serotonin or 5-Hydroxytryptamine (5-HT) is abundantly distributed in the central nervous system, including hippocampus and frontal cortex. 5-HT receptors are a family of G-protein coupled receptors, characterized with 7-transmembrane helices and presently have fourteen known receptor subtypes, some of which exist as multiple splice variants [D. L. Murphy, A. M. Andrews, C. H. Wichems, Q. Li, M. Tohda and B. Greenberg, *J. Clin. Psychiatry*, 1998, 59 (suppl. 15), 4]. 5-HT influences a number of physiological functions and is implicated in a large number of central nervous system disorders, vascular diseases, neurodegenerative diseases and others (Childers, W. E., et. al., *Ann. Rep. Med. Chem.* 2005, 40, 17).

$5\text{-HT}_{2B}$ receptors are widely distributed in mammalian peripheral tissues including lung, heart, pancreas, spleen, prostate, liver, vascular and skeletal muscle, adipose tissue, intestine, ovary, uterus, testis, and in the central nervous system (CNS) including brain and cerebral cortex. $5\text{-HT}_{2B}$ receptors are expressed in pulmonary endothelial and smooth muscle cells in humans. $5\text{-HT}_{2B}$ receptors stimulate calcium release in human endothelial cells from the pulmonary artery (Esteve, J. M., Launay, J. M., Kellerman, O., Maroteaux, L., Functions of serotonin in hypoxic pulmonary vascular remodeling. *Cell Biochem. Biophys*, 2007, 47, 33-44). The receptor was characterized in the rat gastric (fundus) smooth muscle cells initially as the receptor responsible mediating serotonin-induced contraction in this tissue.

Serotonin (5-HT) affects the pulmonary vasculature associated with PAH by vasoconstriction, platelet aggregation, and pulmonary arterial smooth muscle cell proliferation. Serotonin receptors subtypes, $5\text{-HT}_{1B}$, $5\text{-HT}_{2A}$ and $5\text{-HT}_{1B}$ have shown evidence for playing a role in the pathology of PAH. 5-HT2B receptors are expressed in pulmonary endothelial and smooth muscle cells and stimulate calcium release in human endothelial cells from the pulmonary artery. It has been demonstrated that $5\text{-HT}_{2B}$ receptors are involved in the development of PH by mediating chronic hypoxic responses in wild-type mice compared with the complete lack of PH and vascular remodeling in the $5\text{-HT}_{2B}$ receptor (−/−) knockout mice in the chronic hypoxic mouse model of PH (Launey et. al., Function of the serotonin 5-Hydroxytryptamine 2B receptor in pulmonary hypertension. *Nat. Med* 2002, 8, 1129-1135).

$5\text{-HT}_{2B}$ receptor modulators (antagonists, partial agonists, inverse agonists and agonists) have the potential to be selective for diseased pulmonary trachea, thymus, thyroid, salivary gland vasculature (i.e., vessels affected by hypoxic conditions) compared to normal pulmonary and systemic vessels. Due to this selectivity, $5\text{-HT}_{2B}$ modulators particularly $5\text{-HT}_{2B}$ antagonists offer a possible therapeutic advantage over the available agents for the treatment of pulmonary arterial hypertension, pulmonary hypertension associated with chronic obstructive pulmonary disease (COPD), right ventricular hypertrophy and related disease of the lung and vascular system.

Pulmonary hypertension (PH) is a progressive, debilitating and often fatal disease that results from an increase in pulmonary blood pressure associated with abnormal vascular proliferation. PH is estimated to affect 100,000 people worldwide. Pulmonary arterial hypertension (PAH) is an increase in the pulmonary vascular resistance due to vasoconstriction and pulmonary vascular remodeling that result in elevated pulmonary arterial pressure. The cause of idiopathic PAH is unknown. PAH can be developed as a consequence of existing diseases such as chronic obstructive pulmonary disease (COPD) hypoxia, portal hypertension, or HIV infection. PAH is progressive and fatal. The median survival time without treatment in adult PAH patients is 2.8 years after diagnosis, and is only 10 months in children. Although survival rates have improved with new drugs, the prognosis is still poor and development of safer and more effective drugs is needed. Current treatments include systemically administered intravenous and subcutaneous prostacyclin analogs and orally active endothelin receptor antagonists, which mainly cause pulmonary arterial dilation to relieve symptoms. There is only one approved orally active agent for PH available for patients, a non-selective endothelin A and B receptor antagonist which recquires liver toxicity monitoring.

The role of 5-HT$_{2B}$ in pulmonary hypertension was recognized by the observation that there may be a relationship between the PAH patients taking weight reducing agents such as dexfenfluramine, fenfluramine and aminorex which are 5-HT$_{2B}$ agonists; that the use of these agents may be contributing towards the elevation of pulmonary arterial hypertension (Kramer. M. S., and Lane, D. A Aminorex, dexfenfluramine, and primary pulmonary hypertension, *J. Clin. Epidemiol.* 1998, 51, 361-364). Both aminorex and fenfluramine elevates 5-HT levels by increasing the release of 5-HT from platelets and inhibiting the metabolism and the reuptake of 5-HT (Maclean, M. R., Pulmonary hypertension, anorexigens, and 5-HT: pharmacological synergism in action? *Trends Pharmacology. Sci.* 1999, 20, 490-495; Belohlavkova, S., Simok, J., Kokesova, A., Hnilickova, O., Hampl, V., Fenfluramine-induced pulmonary vasoconstriction: role of serotonin receptors and potassium channels. J. Appl. Physiol. 2001, 91, 755-761). Dexfenfluramine has binding affinity for 5-HT$_2$ receptors and its major metabolite, N-deethylated dexfenfluramine is a potent agonist of the 5-HT$_{2B}$ receptor and thus is involved in the development of PAH.

A novel and potent 5-HT$_{2B}$ receptor antagonist, PRX-08066, has been shown to significantly reduce the elevation in pulmonary arterial pressure and right ventricular hypertrophy and also maintains cardiac function. Pulmonary vascular remodeling was also decreased in rats. The 5-HT$_{2B}$ antagonist PRX-08066 was shown to prevent the severity of PAH in the rat model (Porvasnik, S. L., Germain, S., Embury, J., Ganon, K. S., Jacques, V., Murray, J., Byrne, B. J., Shacham, S., Al-Mousily, F., PRX-08066, a novel 5-hydroxytryptamine receptor 2B antagonist, reduces monocrotaline-induced pulmonary arterial hypertension and right ventricular hypertrophy in rats., *J. Pharmaco. Exp. Ther.* 2010, 334, 364-372).

The 5-HT$_{2B}$ receptor has also been shown to play a key role in the regulation of neuroendocrine tumor cell proliferation and the modulation of the fibroblast component of the neoplastic microenvironment (Svejda, B., et. al. *Cancer* 2010, 116, 2902-12). Small intestinal neuroendocrine tumors (SI-NETs) are cancers originating from serotonin-producing enterochromaffin cells in the diffuse neuroendocrine system. The carcinoid syndrome reflects excessive serotonin release. Carcinoid syndrome symptomatology includes bronchoconstriction, flushing, diarrhea, and fibrosis in the local peritumoral tissue and at distant in the heart or lungs. 5-HT shows both mitogenic and fibrogenic effects in fibroblasts, smooth muscle cells, and endothelial cells. These effects are mediated via the G-protein coupled 5-HT receptors, which activate mitogenic pathways through the extracellular signal-regulated kinase (ERK) pathway and JNK activation. Other studies have reported that 5-HT modulates valvular subendocardial cell proliferation. The human heart valves express messenger ribonucleic acid (mRNA) for 5-HT agonists (fenfluramine, dexfenfluramine, pergolide, cabergoline, ergotamine) are associated with pulmonary fibrosis and valvular heart disease (Roth, B., Drugs and valvular heart disease. *N. Engl. J. Med.* 2007, 356, 6-9; Gustafsson, B, Hauso, O., Drozdov, I., Kidd, M., Modlin, I., Cacinoid heart disease. *Int. J. Cardio.* 2008, 129, 318-324). Significant evidence exists for involvement of 5-HT$_{2B}$ receptors in cellular pathways that culminate in fibrosis. It has been recognized that SI-NETs are often present with fibrosis in the peritumoral tissue, the adjacent mesentery and peritoneum as well as in the right side of the heart or lungs (Modlin, I., Moss, S., Chung, D., Jensen, R., Snyderwine, E., Priorities for improving the management of gastroentero-pancreatic neuroendocrine tumors. *J. Natl. Cancer. Inst.* 2008, 100, 1282).

The proliferative activity of 5-HT has been shown to be dependent on the expression of 5-HT$_2$ receptor subtypes (Kidd, M., et. al. Inhibition of proliferation of small intestinal and bronchopulmonary neuroendocrine cell lines by using peptide analogs targeting receptors. *Cancer.* 2008, 112, 1404-1414). Similar proliferation effects have been observed in the 5-HT secreting prostate cancer cell line PC3 (Dizeyi, N., et. al. Expression of serotonin receptors 2B and 4 in human prostate cancer tissue and effects of their antagonists on prostate cancer cell lines. *Eur. Urol.* 2005, 47, 895-900), 5-HT$_{2A}$ receptor expressing breast cancer cell line MCF-7 (Sonier, B., et. al. The 5-HT$_{2A}$ serotoninergic receptor is expressed in the MCF-7 human breast cancer cell line and reveals a mitogenic effect of serotonin. Biochem. Biophys. Res. Commun. 2006, 343, 1053-1059), and in human choricarcinoma cell line JEG-3 and BeWO (Sonier, B., et. al. Expression of the 5-HT$_{2A}$ serotoninergic receptor in human placenta and choriocarcinoma cells: mitogenic implications of serotonin. *Placenta.* 2005, 26, 484-490).

During the investigation of signal transduction pathways involved in the antiproliferative effect of 5-HT$_{2B}$ receptor antagonist, by investigating phosphorylation of ERK, direct role of 5-HT$_2$ receptor subtypes has been demonstrated in vascular and tracheal smooth muscle cell proliferation. The mechanism involves coupling of 5-HT$_{2A}$ receptors and the ERK pathway, while 5-HT$_{2B}$ receptors activate ERK through the RAS pathway (Nebigil, C. G., et. al. 5-hydroxytryptamine 2B receptor regulates cell-cycle progression: cross-talk with tryrosine kinase pathways. *Proc. Natl. Acad. Sci. USA.* 2000, 97, 2591-2596); Hershenson, M. B., et. al. Histamine antagonizes serotonin and growth factor-induced mitogen-activated protein kinase activation in bovine tracheal smooth muscle cells. J. Biol. Chem. 1995, 270, 19908-19913); Banes, A., et. al., Mechanisms of 5-hydroxytryptamine 2A receptor activation of the mitogen-activated protein kinase pathway in vascular smooth muscle. *J. Pharmacol. Exp. Ther.* 1999, 291, 1179-1187).

Fibrosis is an important key feature of small intestinal neuroendocrine tumor (SI-NETs) both in local peritumoral tissue and systemic (cardiac) sites. 5-HT is a well known inducer of fibrosis. The growth factors regulating fibrosis and proliferation in the tumor microenvironment and mechanisms are unclear. It has been shown that blocking 5-HT$_{2B}$ receptors on tumor cells inhibit SI-NET 5-HT release and in turn fibroblast activation in the tumor microenvironment. In the 5-HT$_{2B}$ expressing SI-NET cell line, KRJ-1, the 5-HT$_{2B}$ antagonist PRX-08066 has been shown to inhibit proliferation and 5-HT secretion and decreased ERK1/2 phosphorylation and profibrotic growth factor synthesis and secretion (transforming growth factor beta-1 {TGFβ1}), connective tissue growth factor (CTGF) and fibroblast growth factor (FGF2). The 5-HT2B antagonist PRx-08066 was also found to significantly decrease 5-HT release, TGFβ1, CTGF, and FGF2.

Blocking the 5-HT$_{2B}$ receptor with a 5-HT$_{2B}$ antagonist is an effective antiproliferative and antifibrotic strategy for SI-NETs because it inhibits tumor micronvironment fibroblasts as well as NET cells. Use of 5-HT$_{2B}$ receptor antagonists offers a possible effective therapeutic intervention to prevent tumor progression, fibrosis, and metastasis in the neuroendocrine neoplasia. It may also have therapeutic use in other fibrotic processes associated with neuroendocrine cell dysregulation such as Crohn's disease (Kidd, M., et. al. IL1betaand LPS-induced serotonin secretion is increased in EC cells derived from Crohn's disease. Neurogastroenterol Motil. 2009; 21, 439-450).

The compounds of this invention represented by formula I are valuable in the prevention and treatment of various disease conditions regulated directly or indirectly by the inhibition (by serotonin receptors antagonist of compounds of formula I) or activation (by serotonin receptors partial or full agonist of compounds of formula I) of the neurotransmitter serotonin (5-Hydroxytryptamine, 5-HT). These diseases include cancer such as brain cancer, breast cancer, blood cancer, colorectal cancer, lung cancer, liver cancer, ovarian cancer, pancreas cancer, prostate cancer, stomach cancer, testicular cancer, uterus cancer, intestinal cancer, skin cancer, and other forms of cancer; tumor progression, metastasis and fibrosis in the neuroendocrine neoplasia, fibrotic processes associated with neuroendocrine cell dysregulation for example Crohn's disease, pulmonary arterial hypertension, pulmonary hypertension associated with chronic obstructive pulmonary disease (COPD), right ventricular hypertrophy, pulmonary vascular remodeling, asthma, cystic fibrosis, hypertension, ischemic stroke, angina pectoris, congestive heart failure, arrhythmia, arterial fibrillation, neurodenerative diseases, Alzheimer's disease, dementia, cognition impairment, memory decline, schizophrenia, dementia associated with Parkinson's and Huntington's disease, Pick's disease and Jacob disease.

These compounds may also have applications in the treatment of gastrointestinal disorders including irritable bowel syndrome, gastroesophageal reflux disease, Crohn's disease, gastric emptying disorders, gastritis, emesis, nausea, vomiting, prokinesia, non-ulcer dyspepcia, urinary incontinence, feeding disorders, bulimia, anorexia, obesity, constipation, constipation, and respiratory depression, stress disorders, post-traumatic stress disorder, acute stress disorder, delirium, anxiety, depression, biopolar depression, epilepsy, Down's syndrome, pain, migraine, panic disorders, social phobia, animal phobias, and obsessive compulsive disorders.

The compounds of formula I may also be valuable in substance-related disorders including dependence and abuse, intoxication, withdrawal, and delirium arising from the use of alcohol, amphetamines, cannabis, cocaine, hallucinogens, inhalants, nicotine, opioids, hypnotics, and anxiolytics.

These compounds of formula I may also be useful for the prevention and treatment of demyelinating diseases including multiple sclerosis, ALS, peripheral neuropathy, postherpetic neurolegia, cerebral vascular disorders, acute or chronic cerebrovascular damage, cerebral infarction, subarachanoid hemorrhage, and cerebral edema.

In addition, compounds of the invention may be used for the treatment of bronchoconstriction, vasodilation, smooth muscle contraction, brain disorders, vascular disorders, blood flow disorders as a result of vasodilation and vasospastic diseases such as angina, vascular headache, Reynaud's disease, pulmonary hypertension, and systemic hypertension; neuropathological diseases such as Alzheimer's diseases, Parkinson's disease, Huntington's disease; cardiovascular system regulation, prophylaxis and treatment of cerebral infarct, stroke, cerebral ischemia; as well as the treatment of diseases of the intestinal tract.

The compounds of the present invention may also be useful in the treatment of stress-related somatic disorders, bladder function disorders such as cystitis, stress-related urinary incontinence, urinary incontinence post prostate cancer-surgery, reflex sympathetic dystrophy including shoulder/hand syndrome, bladder function disorders such as cystitis, and any nociception, pain or migraine associated with the above mentioned conditions.

DETAILED DESCRIPTION OF THE INVENTION

This invention is concerned with pyrimidine compounds and their derivatives of the formula I and pharmaceutically acceptable salts thereof,

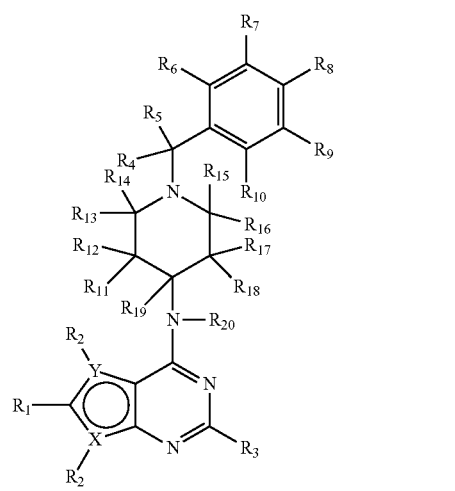

wherein,
when X=S, Y is C or N; when Y is C, it is substituted with $R_2$;
when Y=S, X is C or N; when X is C, it is substituted with $R_2$;
$R_1$ is D (Deuterium), H, F, Cl;
$R_2$ is D, H, F, Cl;
$R_3$ is H, D;
$R_4$ and $R_5$ are D, H;
$R_6$, $R_7$, $R_8$, $R_9$ and $R_{10}$ are D, H, F, Cl, CN;
$R_{11}$, $R_{12}$, $R_{13}$, $R_{14}$, $R_{15}$, $R_{16}$, $R_{17}$, $R_{18}$, and $R_{19}$ are D, H;
$R_{20}$ is D, H;
and salts thereof.

Pharmaceutically acceptable salts selected from the group consisting of hydrochloride, acetate, trifluoroacetate, mesylate, maleate, broselate, fumarate, maleic, malic, citrate, tartrate, sodium, potassium, calcium and magnesium salts. The compounds of formula I have antagonist or agonist activity for serotonin receptor subtypes 2B (5-HT$_{2B}$ receptor), 5-HT$_{1A}$ and dopamine receptors, and these compounds and pharmaceutical salts thereof can accordingly be used for the treatment of diseases associated with these receptors, especially cancer including brain cancer, breast cancer, blood cancer, colorectal cancer, lung cancer, liver cancer, ovarian cancer, pancreas cancer, prostate cancer, stomach cancer, testicular cancer, uterus cancer, intestinal cancer, skin cancer, and other forms of cancer; tumor progression, metastasis and fibrosis in the neuroendocrine neoplasia, fibrotic processes associated with neuroendocrine cell dysregulation for example Crohn's disease, pulmonary arterial hypertension, pulmonary hypertension associated with chronic obstructive pulmonary disease (COPD), right ventricular hypertrophy, pulmonary vascular remodeling, asthma, cystic fibrosis, hypertension, ischemic stroke, angina pectoris, congestive heart failure, arrhythmia, arterial fibrillation, neurodegenerative diseases, Alzheimer's disease, dementia, cognition impairment, memory decline, schizophrenia, dementia associated with Parkinson's and Huntington's disease, Pick's disease and Jacob disease, gastrointestinal disorders including irritable bowel syndrome, gastroesophageal reflux disease, Crohn's disease, gastric emptying disorders, gastritis, emesis, nausea, vomiting, prokinesia, non-ulcer dyspepsia, urinary incontinence, feeding disorders, bulimia, anorexia, obesity, constipation, constipation, and respiratory depression, stress disorders, post-traumatic stress disorder, acute stress disorder, delirium, anxiety, depression, biopolar depression, epilepsy, Down's syndrome, pain, migraine, panic disorders, social phobia, animal phobias, and obsessive compulsive disorders, substance-related disorders including dependence and abuse, intoxication, withdrawal, and delirium arising from the use of alcohol, amphetamines, cannabis, cocaine, hallucinogens, inhalants, nicotine, opioids, hypnotics, and anxiolytics, demyelinating diseases including multiple sclerosis, ALS, peripheral neuropathy, postherpetic neurolegia, cerebral vascular disorders, acute or chronic cerebrovascular damage, cerebral infarction, subarachanoid hemorrhage, and cerebral edema, bronchoconstriction, vasodilation, smooth muscle contraction, brain disorders, vascular disorders, blood flow disorders as a result of vasodilation and vasospastic diseases such as angina, vascular headache, Reynaud's disease, pulmonary hypertension, and systemic hypertension; neuropathological diseases such as Alzheimer's diseases, Parkinson's disease, Huntington's disease; cardiovascular system regulation, prophylaxis and treatment of cerebral infarct, stroke, cerebral ischemia; as well as the treatment of diseases of the intestinal tract, stress-related somatic disorders, bladder function disorders such as cystitis, stress-related urinary incontinence, urinary incontinence post prostate cancer-surgery, reflex sympathetic dystrophy including shoulder/hand syndrome, bladder function disorders such as cystitis, and any nociception, pain or migraine associated with the above mentioned conditions.

A preferred group of compounds of formula I are those in which,

I when X=S, Y is C or N; when Y is C, it is substituted with $R_2$;
when Y=S, X is C or N; when X is C, it is substituted with $R_2$;

$R_1$ is D (Deuterium, 1%-100% enrichment of deuterium is incorporated), F, Cl;
$R_2$ is D, Cl;
$R_3$ is H, D;
$R_4$ and $R_5$ are D, H;
$R_6$, $R_9$ and $R_{10}$ are D, H;
$R_7$ is CN;
$R_8$ is F;
$R_{11}$, $R_{12}$, $R_{17}$, $R_{18}$, and $R_{19}$ are D;
$R_{13}$, $R_{14}$, $R_{15}$, $R_{16}$,
$R_{20}$ is D;
and salts thereof.

One of the objectives of the present invention is to provide deuterium enriched compounds of formula I or a pharmaceutically acceptable salt thereof.

It is another objective of the present invention to provide pharmaceutical compositions comprising a pharmaceutically acceptable carrier and a therapeutically effective amount of at least one of the deuterium enriched compounds of the present invention a pharmaceutically acceptable salt thereof.

It is another object of the present invention to provide a method for the prevention and treatment of cancer including cancer such as brain cancer, breast cancer, blood cancer, colorectal cancer, lung cancer, non-small cell lung cancer, liver cancer, ovarian cancer, pancreas cancer, prostate cancer, stomach cancer, testicular cancer, uterus cancer, intestinal cancer, skin cancer, and other forms of cancer.

Another aspect of the invention is to provide a method for the prevention and treatment of tumor progression in various cancers mentioned above.

Another aspect of the invention is to provide a method for the prevention and treatment of metastasis of cancer tumors in various forms of cancer mentioned above.

Another aspect of the invention is to provide a method for the prevention and treatment of fibrosis in the neuroendocrine neoplasia.

Another aspect of the invention is to provide a method for the prevention and treatment of fibrotic processes associated with neuroendocrine cell dysregulation for example Crohn's disease.

It is another object of the present invention to provide a method for the prevention and treatment of pulmonary arterial hypertension.

It is another object of the present invention to provide a method for the prevention and treatment of right ventricular hypertrophy.

It is another object of the present invention to provide a method for the prevention and treatment of pulmonary vascular remodeling.

It is another object of the present invention to provide a method for the prevention and treatment of hypertension, angina pectoris, and congestive heart failure.

It is another object of the present invention to provide a method for the prevention and treatment of all disease regulated directly or indirectly by 5-HT receptors, comprising administering to a host in need of such treatment a therapeutically effective amount of at least one of the compounds of the present invention or a pharmaceutically acceptable salt thereof.

It is another object of the present invention to provide a novel deuterium-enriched pyrimidine compounds of formula I, pharmaceutically acceptable salts thereof for use as therapeutic agents.

It is another object of the present invention to provide a novel deuterium-enriched pyrimidine compounds of formula I, pharmaceutically acceptable salts thereof for use as prophylactic agent.

It is another object of the present invention to provide a novel deuterium-enriched pyrimidine compounds of formula I, pharmaceutically acceptable salts thereof for use as therapeutic agents administered as a single therapeutic agent or given in combination with another clinically approved therapeutic agent.

It is another objective of the present invention to provide the use of a novel compound of formula I or a pharmaceutically acceptable salt thereof for the manufacture of a medicine for the treatment of cancer, fibrosis, pulmonary arterial hypertension, resistant hypertension, hypertension, congestive heart failure, and male erectile dysfunction, anxiety, Alzheimer's, Parkinson's, and Huntington's disease.

Also provided are various deuterium-enriched compounds of formula I and administering those compounds to a subject in need thereof to treat or prevent a disease condition that is alleviated by treatment with a 5-$HT_{2B}$ (and/or all 5-HT) receptor antagonist, dopamine receptor modulators. Disease conditions that are alleviated by treatment with 5-HT modulators particularly 5-$HT_{2B}$ receptor antagonists include, but are not limited to, e.g., cancer including brain cancer, breast cancer, blood cancer, colorectal cancer, lung cancer, liver cancer, ovarian cancer, pancreas cancer, prostate cancer, stomach cancer, testicular cancer, uterus cancer, intestinal cancer, skin cancer, and other forms of cancer; tumor progression, metastasis and fibrosis in the neuroendocrine neoplasia, fibrotic processes associated with neuroendocrine cell dysregulation for example Crohn's disease, pulmonary arterial hypertension, pulmonary hypertension associated with chronic obstructive pulmonary disease (COPD), right ventricular hypertrophy, pulmonary vascular remodeling, asthma, cystic fibrosis, hypertension, ischemic stroke, angina pectoris, congestive heart failure, arrhythmia, arterial fibrillation, neurodegenerative diseases, Alzheimer's disease, dementia, cognition impairment, memory decline, schizophrenia, dementia associated with Parkinson's and Huntington's disease, Pick's disease and Jacob disease, gastrointestinal disorders including irritable bowel syndrome, gastroesophageal reflux disease, Crohn's disease, gastric emptying disorders, gastritis, emesis, nausea, vomiting, prokinesia, non-ulcer dyspepcia, urinary incontinence, feeding disorders, bulimia, anorexia, obesity, constipation, constipation, and respiratory depression, stress disorders, post-traumatic stress disorder, acute stress disorder, delirium, anxiety, depression, biopolar depression, epilepsy, Down's syndrome, pain, migraine, panic disorders, social phobia, animal phobias, and obsessive compulsive disorders, substance-related disorders including dependence and abuse, intoxication, withdrawal, and delirium arising from the use of alcohol, amphetamines, cannabis, cocaine, hallucinogens, inhalants, nicotine, opioids, hypnotics, and anxiolytics, demyelinating diseases including multiple sclerosis, ALS, peripheral neuropathy, postherpetic neurolegia, cerebral vascular disorders, acute or chronic cerebrovascular damage, cerebral infarction, subarachanoid hemorrhage, and cerebral edema, bronchoconstriction, vasodilation, smooth muscle contraction, brain disorders, vascular disorders, blood flow disorders as a result of vasodilation and vasospastic diseases such as angina, vascular headache, Reynaud's disease, pulmonary hypertension, and systemic hypertension; neuropathological diseases such as Alzheimer's diseases, Parkinson's disease, Huntington's disease; cardiovascular system regulation, prophylaxis and treatment of cerebral infarct, stroke, cerebral ischemia; as well as the treatment of diseases of the intestinal tract, stress-related somatic disorders, bladder function disorders such as cystitis, stress-related urinary incontinence, urinary incontinence post prostate cancer-surgery, reflex sympathetic dystrophy including shoulder/hand syndrome, bladder function disorders such as cystitis, and any nociception, pain or migraine associated with the above mentioned conditions.

The present invention relates to compounds of formula I, their pharmaceutically acceptable salts, compositions and their use as mono therapy or in combination with existing therapies.

Deuterium (D or $^2H$) is a stable isotope non-radioactive isotope of hydrogen (H) and has an atomic weight of 2.0144. Hydrogen occurs naturally as a mixture of the isotopes $^1H$, D (H2), and T ($^3H$ or tritium) and the natural abundance of deuterium is 0-0.0156%. One of ordinary skill in the art recognizes that in all compounds containing H atom, H actually represents a mixture of H and D, with about 0-0.0156% of D. So, compounds with a level of D that has been enriched to be greater than its natural abundance of 0.0156%, should be considered unnatural and as a result novel as compared to their corresponding non-enriched counterparts.

The carbon-hydrogen bonds contain a naturally occurring distribution of hydrogen isotopes, namely $^1H$ or protium (about 99.9844%), $^2H$ or deuterium (D) (about 0.0156%), and $^3H$ or tritium (in the range between about 0.5 and 67 tritium atoms per $10^{18}$ protium atoms). Higher levels of deuterium incorporation produce a detectable Kinetic Isotope Effect (Werstiuk, N. H.; Dhanoa, D. S.; Timmins, G. Can J. Chem. 1979, 57, 2885; Werstiuk, N. H.; Dhanoa, D. S.; Timmins, G. Can J. Chem. 1983, 61, 2403), that could improve the pharmacokinetic, pharmacologic and/or toxicologic parameters of compounds of formula I in comparison to compounds having naturally occurring levels of deuterium and their corresponding hydrogen (protium) analogs. Deuterium as an isostere of hydrogen has been employed in drug design (Meanwell, N. A., Synopsis of some recent tactical applications of bioisosteres in drug design., *J. Med. Chem.* 2011, 54, 2529-2591).

The present invention disclosed herein describes novel compounds of formula I containing higher content of deuterium (>1%), synthesis and uses thereof as 5-HT receptor antagonists and/or inverse agonist for the treatment of diseases in which 5-HT plays role directly or in directly. Suitable modifications of certain carbon-hydrogen bonds into carbon-deuterium bonds generates novel substituted pyrimidine compounds with unexpected and non-obvious improvements of pharmacological, pharmacokinetic and toxicological properties in comparison to the non-isotopically enriched 5-$HT_{2B}$ antagonists, agonists, or inverse agonists. This invention relies on the judicious and successful application of chemical kinetics to drug design. Deuterium incorporation levels in the compounds of the invention are significantly higher than the naturally-occurring levels and are sufficient to induce at least one substantial improvement as described herein. All percentages given for the amount of D present are mole percentages.

"Deuterium enrichment" refers to the percentage of incorporation of deuterium at a given site on the molecule instead of a hydrogen atom. For example, deuterium enrichment of 1% means that in 1% of molecules in a given sample a particular site is occupied by deuterium. Because the naturally occurring distribution of deuterium is about 0.0156%, deuterium enrichment in compounds synthesized using non-enriched starting materials is about 0.0156%.

It can be a significant synthetic challenge to produce 100% deuterium at a specific site of a compound. When 100% deuteration is recited or a deuterium atom is specifically shown in a chemical structure of a compound, a small amount of deuterium may still be present. Higher levels of deuterium content in a compound can be produced either by Hydrogen-Deuterium (H-D) exchange or by synthesizing the compound for specific deuteration. The H-D exchange is readily achieved in case of H atoms attached to heteroatoms for example in cases of carboxylic acids (COOH), sulfonamides (SO$_2$NH$_2$), alcohols (OH), basic amines (NH$_2$), etc. However, these incorporated D attached to hetero atoms (O, N, S) etc, readily revert back to H upon exposure to water or any acidic compounds containing H atoms. The preferred deuterium containing compounds are the ones which contain D directly attached to carbon atoms of the structure of the compounds of this invention.

In some embodiments, the deuterium enrichment in the compounds of the present invention is greater than 4%, 5%, 6%, 7%, 8%, 9% or 10%. In other embodiments, the deuterium enrichment in the compounds of the present invention is greater than 20%. In further embodiments, the deuterium enrichment in the compounds of the present invention is greater than 50%. In some embodiments, the deuterium enrichment in the compounds of the present invention is greater than 70%. In some embodiments, the deuterium enrichment in the compounds of the present invention is greater than 90%.

The examples provided in the definitions present in this application are non-inclusive unless otherwise stated. They include but are not limited to recited examples. The compounds of the present may have various isomers including all stereoisomers of asymmetric atoms and geometric, tautomeric or rotamers, and all isomers are considered to be part of the present invention. All processes used to prepare compounds of the present invention and intermediates made therein are considered to be part of the present invention.

"Pharmaceutically acceptable salts" refer to derivatives of the disclosed compounds wherein the parent compound is modified by making acid or base salts thereof. Examples of the pharmaceutically acceptable salts include, but not limited to, mineral or organic acid salts of the basic residues. The pharmaceutically acceptable salts include but not limited to HCl, HBr, HI, acetic, trifluoroacetic, citric, ascorbic, benzoin, methanesulfonic, benzenesulfonic, bicarbonic, carbonic, ethane disulfonic, edetic, fumaric, maleic, lactic, malic, mandelic, gluconic, glutamic, glycolic, glycollyarsanilic, lauryl, hexylresorcinic, hyrdabamic, hydroxymaleic, hydroxynaphthoic, isethionic, lactobionic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, tolouenesulfonic, and p-bromobenzenesulfonic.

The preparation of pyrimidine compounds of formula I are illustrated in schemes 1-8 below and in the examples given in Table 1. The schemes and examples are given for the purpose of illustrating the invention and not for limiting the scope or spirit of the invention.

Step A: To a solution of acetaldehyde-d$_4$ 1 (1.2 g) in toluene is added 1.2 equivalent of ethyl cyanoacetate (3.2 g) and ammonium acetate (2.2 g) followed by acetic acid (15 mL). The mixture is refluxed for 6 h under nitrogen using Dean-Stark apparatus. After cooling to room temperature by allowing it to stand, the reaction mixture is concentrated using rotary evaporator under vacuum to remove solvent. To the concentrated residue, is added water and the adduct product 2 is extracted with ethyl acetate. The combined organic layer is dried over anhydrous sodium sulfate or anhydrous magnesium sulfate and concentrated under vacuum. The resulting product 2 (3.0 g) obtained as such is used in step B.

Step B: Morpholine is added to 2 (3 g) in ethanol (5 mL) followed by addition of sulfur in slight excess under nitrogen atmosphere and the suspension is refluxed with stirring for 12 h. After cooling to room temperature, the reaction mixture is concentrated in vacuum and the product 3 is extracted with ethyl acetate from acqueous phase. The combined organic layer was dried over anhydrous sodium sulfate, filtered and the filtrate is concentrated in vacuum and then purified by flash column chromatography using mixture of ethyl acetate and hexane to yield Ethyl 2-Aminothiophene-3-carboxylate-d$_2$ 3 (2.6 g). Mass spectral analysis (MS): m/z: 173.5.

Step C: The ester 3 (0.88 mg) is heated at reflux with deutero ammonium acetate-d$_1$ (100 mg) in 3 ml of formic acid for 8 hrs. The mixture is poured onto ice and the resulting material is filtered and recrystalized from acetone water to give hydroxypyrimidine 4 (0.6 g). Mass spectral analysis (MS): m/z 155.

Step D: The deuterothienopyrimidinol 4 (2 mmol) is heated in thionyl chloride with catalytic amount of N,N-dimethylformamide for 5 hours. The mixture is allowed to cool to room temperature and the excess thionyl chloride is removed under reduced pressure. Excess of ice is added to the mixture and product extracted with dichloromethane. The extracts are dried with anhydrous sodium sulfate, filtered, concentrated and the product purified by flash chromatography over silica gel to yield 5 (0.5 g). Mass spectral analysis (MS): m/z 173.

Step E: To a solution of pyrimidine derivative 5 (0.5 g) was added deuterated acetic acid-d$_4$ (20 mL) and N-chlorosuccinimide (0.2 g) and the mixture was heated for 2.5 h. The reaction mixture was cooled to room temperature and removed acetic acid-d$_4$ in vacuum and the residue was treated with aqueous sodium hydroxide and extracted with dichloromethane. The combined organic extracts were dried over anhydrous MgSO$_4$, filtered and concentrated before purification by flash column chromatography to isolate the 2,6-dichlorothienopyrimidine 6 (0.4 g). Mass spectral analysis (MS) m/z: 205.9.

Scheme 1:

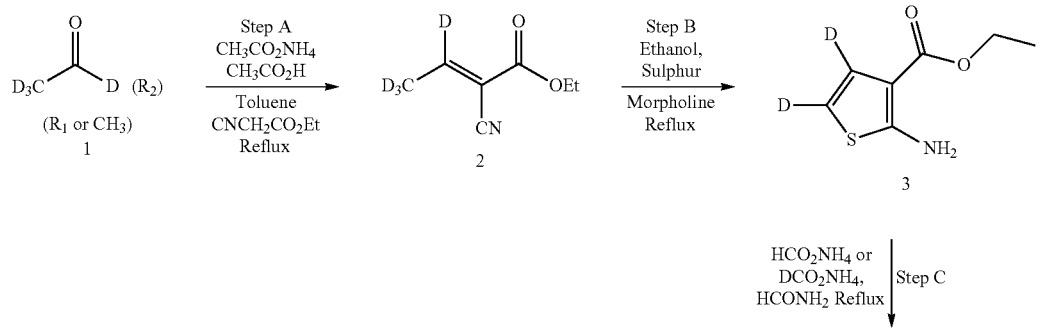

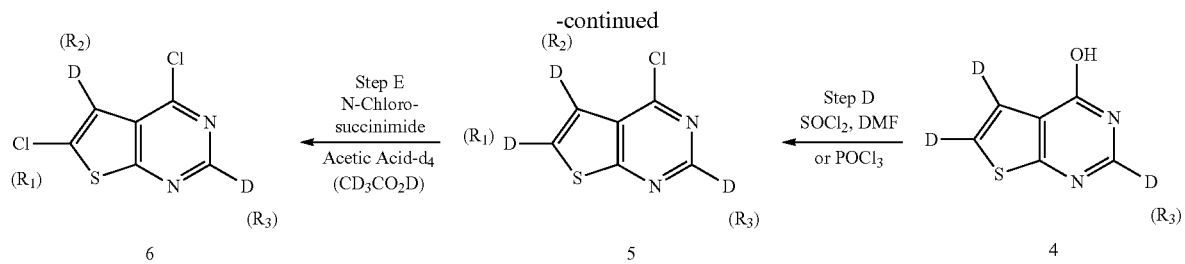

The regioisomeric thienopyrimidine 12 is prepared from deuterated acetaldehyde-d4 as illustrated in Scheme 2.

Step F: To acetaldehyde 7 (0.48 g), DMF, and phosphorus oxychloride (1.2 equiv) is added and the mixture stirred for 5 minutes. Hydroxylamine (1.2 equivalent) is added to the reaction mixture and heated at 50 degree C. for 5 hours. The reaction mixture is cooled to room temperature and poured over to ice. The compound is extracted with methylene chloride and the extracts are dried over anhydrous magnesium sulfate or sodium sulfate, filtered and concentrated under vacuum. The crude product is purified by flash column chromatography to give 8 (0.62 g). MS: m/z 90 (M+1).

Step G: Methyl thioglycolate (1.1 g) and sodium methoxide (2 equiv) in methanol are added to 8 (0.62 g) and the mixture refluxed for 6 hours. The mixture is cooled to room temperature, concentrated to remove solvent and the resulting mixture partitioned between methylene chloride and water. The aqueous portion is further extracted with dichloromethane and ethyl acetate. The combined organic extracts are dried over anhydrous sodium sulfate, filtered and concentrated to a residue. Flash column chromatography of the residue afforded an amino ester 9 (0.8 g).

The intermediate 9 was converted to the pyrimidine derivatives 10, 11 and 12 by using methods describes in Step C, Step D, and Step E, respectively.

Similarly, the amino ester of thiazole, 13, was converted to the 4-hydroxythiozolylpyrimidine 14 and 4-chlorothiazolylpyrimidine 15 as illustrated in Scheme 3 below using step C and Step D as described above.

Scheme 3:

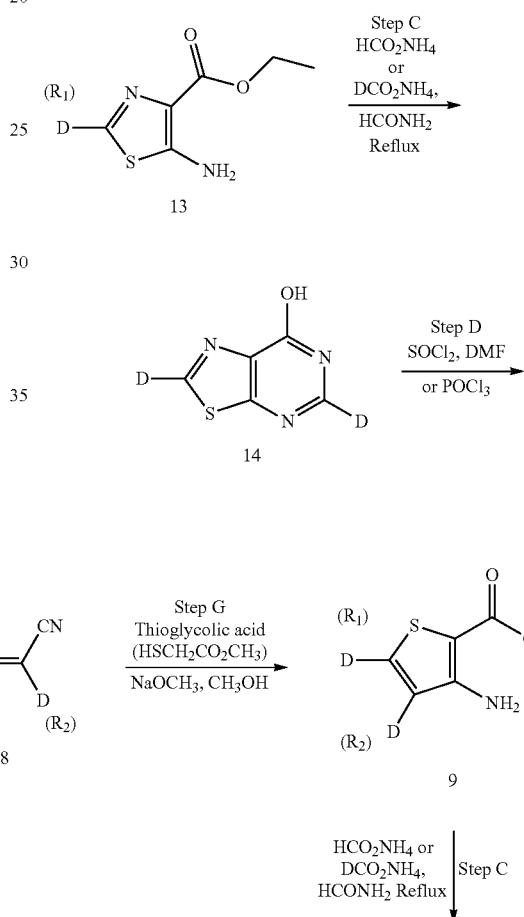

Scheme 2:

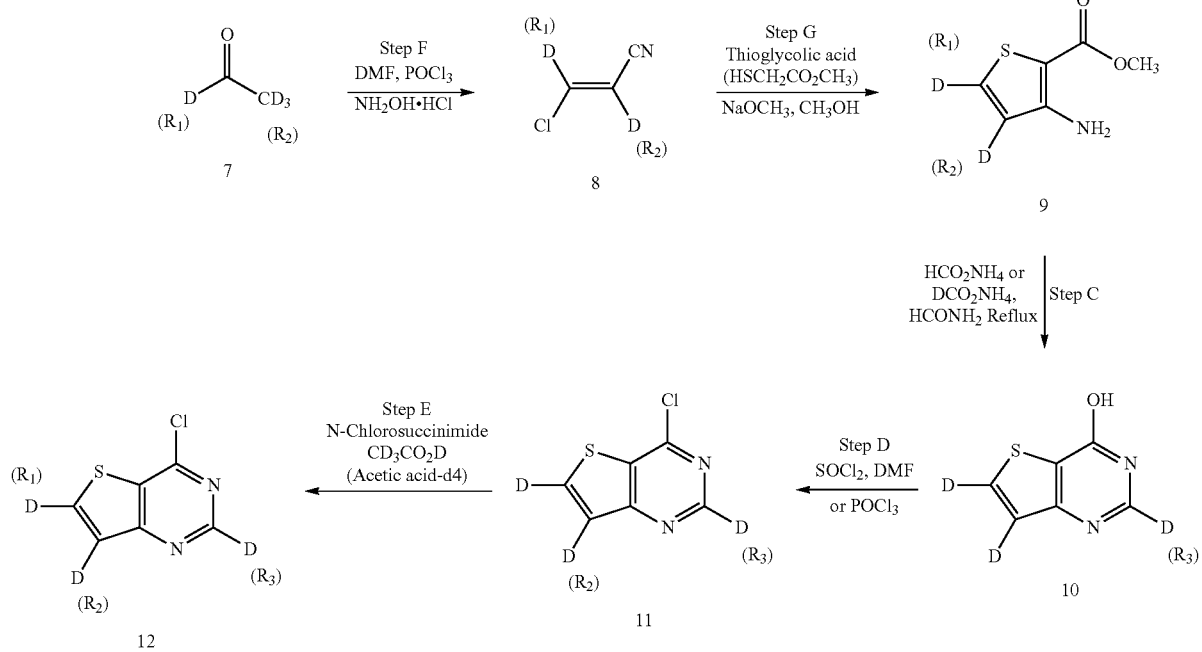

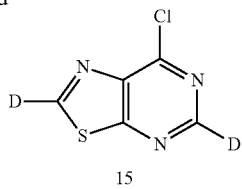

15

Furthermore, the regioisomeric thiazolylpyrimidine 18 is prepared from the corresponding deuterated amino ester 16 as illustrated in Scheme 4 below by utilizing the reaction steps C and D.

Scheme 4:

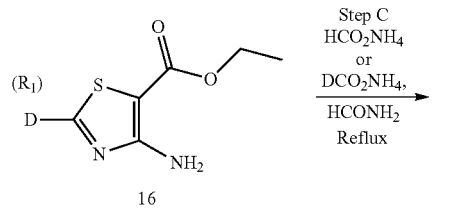

16

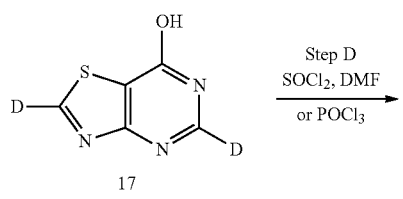

17

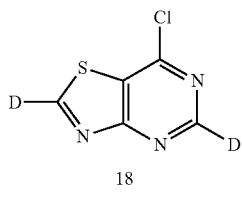

18

Step F: One of three key building blocks of the compounds of formula I of the present invention is the partially or fully deuterated 4-N-Boc-aminopiperidine 20. The preparation of 20 is illustrated in scheme 5 below that employs the use of the reaction step F. The 4-N-Boc-piperidinone is converted to the corresponding amine by reductive amination of 19 with ammonium acetate ($NH_4OAc$) using either sodium triacetoxy borodeuteride [$NaBD(OAc)_3$], or sodium borotetradeuteride [$NaBD_4$], or sodium cyanoborodeuteride [$NaBD_3CN$], as reducing agents in dicholoroethane or dicholoromethane or DMF or tetrahydrofuran (THF) and water ($H_2O$). To a solution of 0.2 g of 4-N-Boc-(2,2,6,6-tetradeuteropiperidinone) 19 ($R_{11}$, $R_{12}$, $R_{17}$, $R_{18}$ are D; $R_{13}$, $R_{14}$, $R_{15}$, $R_{16}$ are H) in DCE and AcOH is added [2 equiv of $NaBD(OAc)_3$] and the reaction mixture stirred for 2 h. The mixture was concentrated and basified with $NaHCO_3$ and saturated with NaCl and the resulting mixture is extracted with methylene chloride. The organic solvent extracts were concentrated in vacuo and the product isolated by flash column chromatography to yield 20 (0.12 g).

Scheme 5:

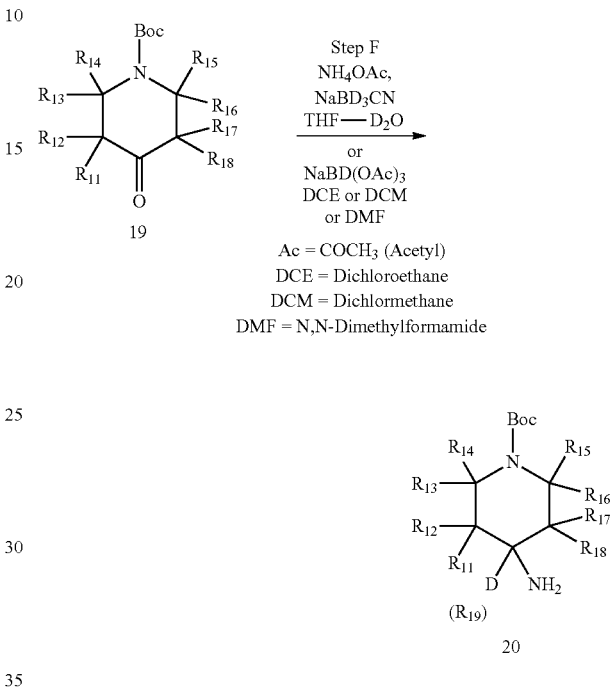

Step G: Diisopropyl ethylamine (Hunigs base) is added to a solution of 4-N-Boc-aminopiperidine-$d_5$, 20 (0.22 g) in acetonitrile (3 ml) followed by addition of 6 (1 equiv). The reaction mixture is refluxed for 24 h. Acetonitrile is removed in vacuo and the resulting residue is dissolved in ethyl acetate (25 ml) and the solution washed with aqueous (aq.) saturated solution of sodium bicarbonate and saturated aqueous solution of sodium chloride (brine). The organic phase is dried over anhydrous $MgSO_4$, concentrated in vacuo and purified by flash column chromatography to give N-Boc protected 21, which in turn is treated with TFA in $CH_2Cl_2$ for 2-3 h or with HCl in ether for 12 h to give the crude amine 21. The mixture containing 21 is concentrated in vacuo, treated the residue with aqueous $NaHCO_3$ solution and aqueous solution of NaCl. The organic product was extracted with ethyl acetate and dicholoromethane and the combined organic solvent extracts washed with brine, dried over anhydrous MgSO4, filtered and concentrated in vacuo. The resulting material is purified to afford 21 (0.15 g). MS: m/z 276 (M+1).

Similarly, the regioisomeric thienopyrimidine 22 (m/z 276 M+1) is prepared from 12 and 20 by using Step H. The regioisomeric thiazolylpyrimidines, 23 (m/z 278 M+1) and 24 (m/z 278 M+1) are also prepared in a similar manner by using Step I and Step J from their precursors 15 and 20, and 18 and 20, respectively as illustrated in Scheme 6.

Scheme 6:
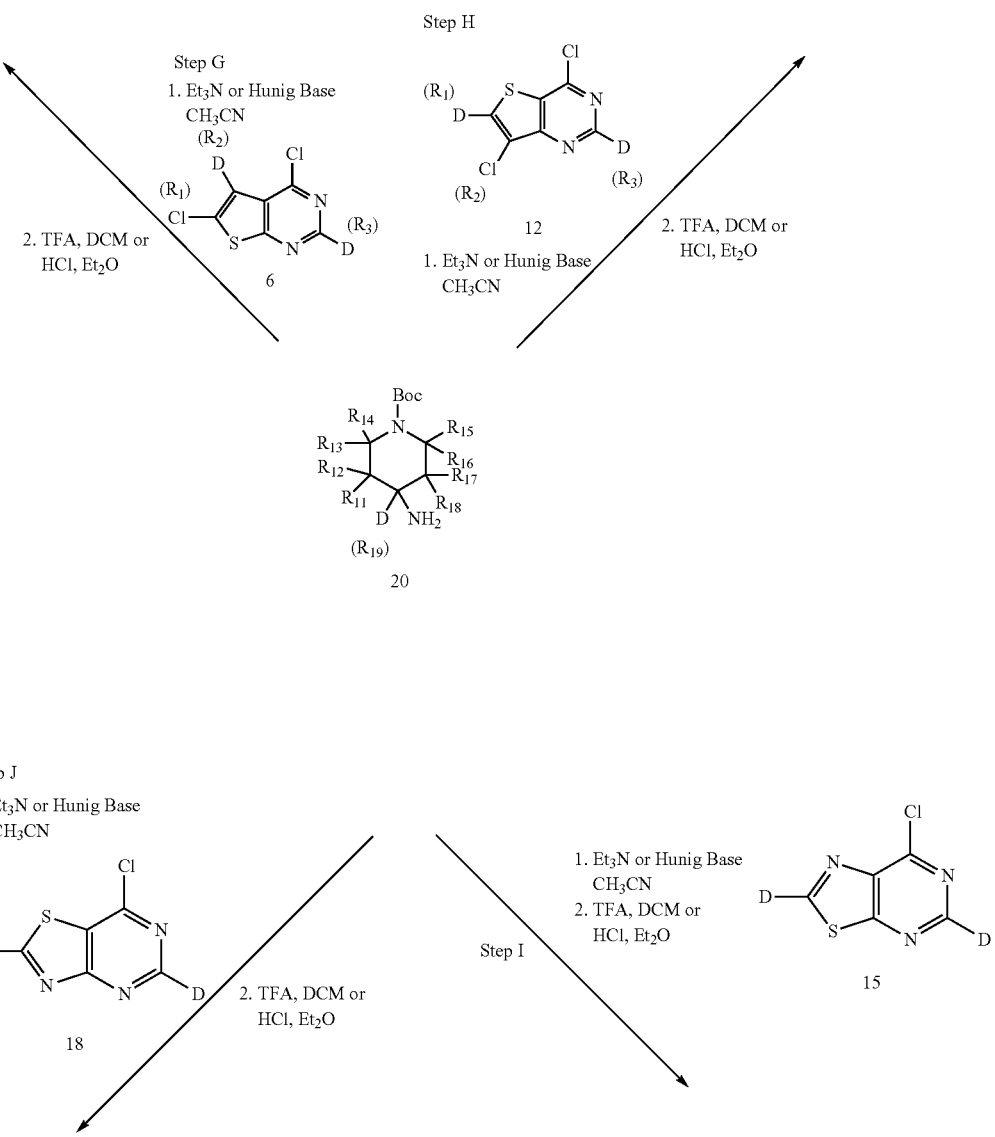

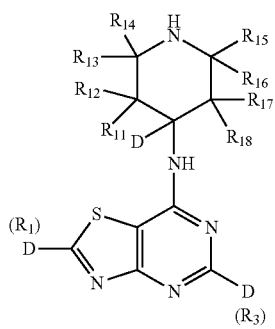

24

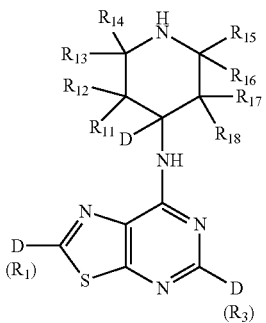

23

Step K: The 4-aminopiperidine-2-chlorothienopyrimidines 21 and 22 are also prepared from the corresponding N-Boc derivatives 25 and 26, respectively as shown in Scheme 7 by step K as described in Step E of scheme 1.

Scheme 7:

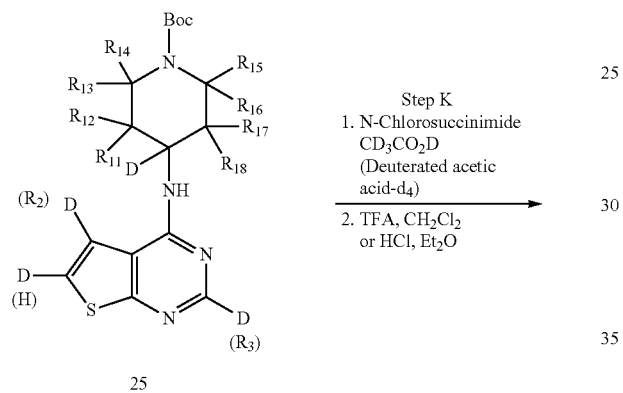

25

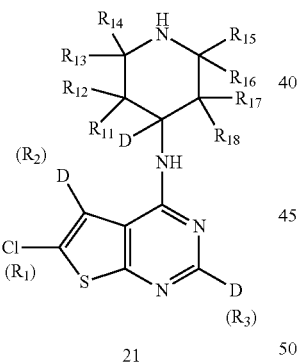

21

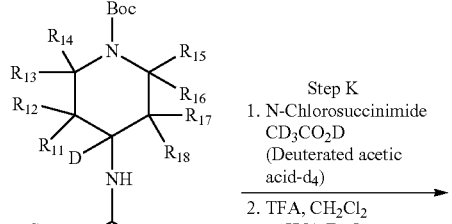

26

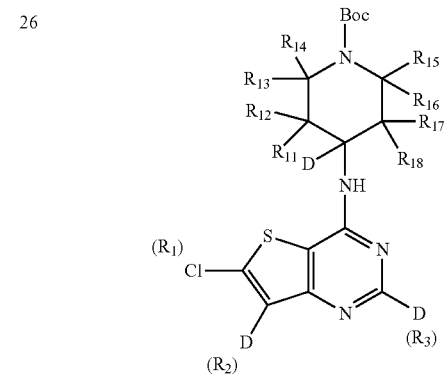

22

Step L: The third key structural moiety of the compound of the present invention comprise the deuterated 3-cycano-4-fluorobenzyl derivatives aldehydes 29 and 30 and aryl bromide 32. Preparation of these compounds is shown in Scheme 8 below.

Scheme 8:

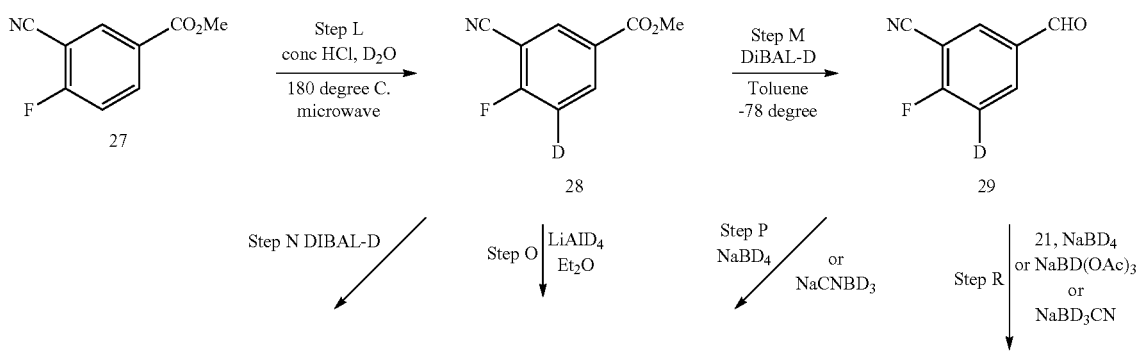

-continued
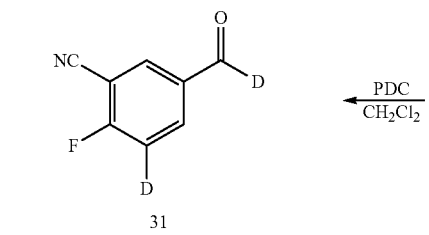 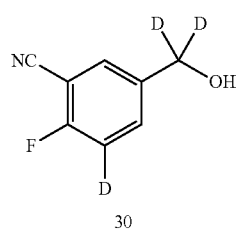 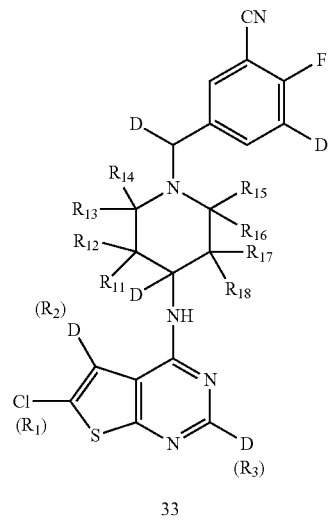
31  30  33
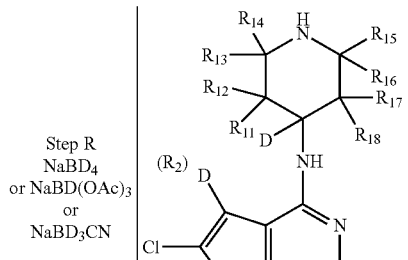
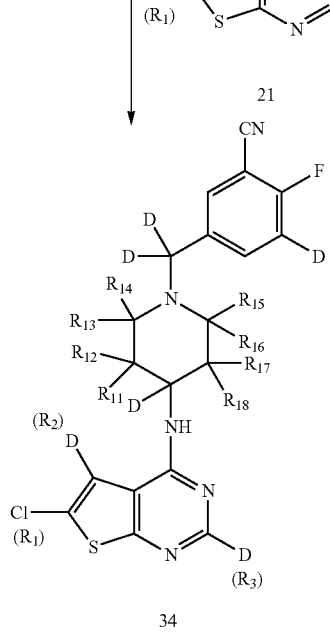 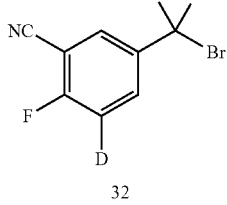
34  32
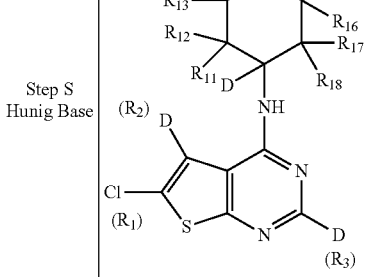
21
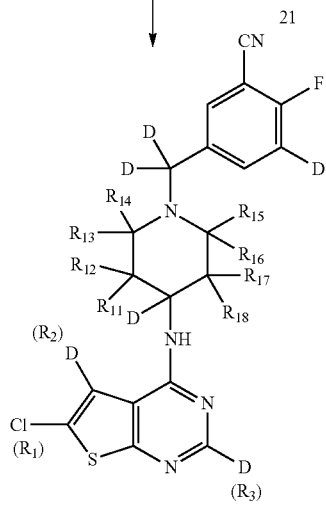
34

Methyl 3-cyano-4-fluorobenzoate 27 (1.8 g) is deuterated by heating with 1 equiv of $D_2O$ and conc. HCl at 180 degree C. under microwave irradiation for 30 minutes (Martin A.; Lautens M., Org. Lett. 2008, 10, 4351-4353). The reaction mixture is basified with aqueous solution of $NaHCO_3$ and extracted with ether. The combined ethereal extracts are concentrated, dried, filtered to and concentrated in vacuo. The concentrated oil is flash chromatogarphed to afford the mono-deuterated 28 (1.62 g).

28 is converted to aldehyde 29 by reducing with diisobutyl aluminum hydride (DIBALH) or diisobutyl aluminum deuteride (DIBALD) in toluene and converted to 31 by treating 28 with DIBALD in toluene at −78 C.

Step M: To a toluene solution of deuterated ester 28 (0.8 g) cooled to −78 C by placing the reaction flask in dry ice-acetone mixture, is added 1.1 equiv of DIBALH or DIBALD and the mixture stirred for 1 hour and quenched methanol and sodium hydroxide. The aqueous phase is extracted with solvent mixture of ether and ethyl acetate, dried extracts over $MgSO_4$, filtered and concentrated in vacuo to an oil which after flash column chromatography gave 29 (0.53 g).

Step N: To a solution of deuterated ester 28 (0.8 g) in toluene cooled to −78 C is added 1.1 equiv of DIBALD and the mixture stirred for 1 hour. Methanolic sodium hydroxide is added to reaction mixture and the aqueous phase is extracted with solvent mixture of ether and ethyl acetate, dried extracts over $MgSO_4$, filtered and concentrated in vacuo to an oil which after flash column chromatography gave 31 (0.55 g).

Step O: To a solution of deuterated ester 28 (0.8 g) in ether cooled to −78 C is added 1.1 equiv of $LiAlD_4$ and the mixture stirred for 1 hour. Aqueous NaOH is added to reaction mixture and stirred for 30 min and then the aqueous phase is extracted with ether and ethyl acetate, dried extracts over $MgSO_4$, filtered and concentrated in vacuo to an oil which after flash column chromatography gave 30 (0.5 g).

Step P: To a solution of 29 (0.5 g) in THF cooled to −78 C is added 1.2 equiv of $NaBD_4$ and the mixture stirred for 1 hour. Methanolic sodium hydroxide is added to reaction mixture and the aqueous phase is extracted with ether and ethyl acetate, dried extracts over anhydrous $MgSO_4$, filtered and concentrated in vacuo to an oil which after flash column chromatography afforded 30 (0.36 g).

Step Q: To a solution of 30 (0.86 g) in dichloromethane at 0 degree is added carbon tetrabromide (1.1 equiv) and stirred. After 5 min, triphenyl phosphine (1 equiv) is added and the resulting mixture stirred for 1 h at 0 degree and allowed to warm to room temperature. The mixture treated with methanol and the mixture concentrated in vacuo, then purification by flash column chromatography gave the tri-deuterated aryl bromide 32 (0.66 g).

The substituted deuterated benzyl bromide 30 can also be converted to the corresponding deuterated aldehyde 31 by its oxidation with PDC (pyridinium dichromate) in methylene chloride in the presence of dry molecular sieves.

Step R: To a mixture of 21 (0.3 g) and deuterated aldehyde 29 is added DCE and $NaBD(OAc)_3$ (1.5 equiv) and deuterated acetic acid-$d_4$ (2 equiv). The reaction mixture is stirred for 12 h at room temperature before the addition of aqueous $NaHCO_3$ solution. The product is extracted with ethyl acetate, dried over anhydrous $MgSO_4$, filtered and concentrated in vacuo to give an oil which is then purified by flash column chromatography to yield the final compound 33 (0.36 g).

The compound 34 is prepared from the aldehyde 31 by using the procedure described in step R.

Step S: To a solution of 21 (0.28 g) and 0.4 ml of diisopropylethylamine (Hunigs base) in 3 ml of $CH_3CN$ is added 32 and the resulting mixture was heated at 85° C. with stirring for 12 h. The mixture is cooled to room temperature and poured over to aqueous sodium bicarbonate solution. The mixture is extracted with ethyl acetate and the combined organic extracts are dried over sodium sulfate, filtered and concentrated in vacuo. The residue is purified by flash column chromatography to give 34 (0.3 g).

To prepare the fully deuterated (or per-deuterated) aldehyde or bromide analogs of 29, 31 and 32, the fully deuterated precursor 38 is prepared from the corresponding aniline 35 as illustrated in Scheme 9 below.

Step T: Methyl 3-amino-4-fluorobenzoate 35 (1.7 g) is heated with 1 equiv of conc HCl and $D_2O$ at 180° C. under microwave irradiation for 30 minutes. The mixture is cooled to room temperature and treated with methanol and basified with aqueous solution of $NaHCO_3$. The mixture is extracted with ether/ethyl acetate mixture, washed combined organic extracts with brine, dried over sodium sulfate, filtered and concentrated in vacuo. The crude product is purified by flash column chromatography to yield di-deuterated aniline 36 (1.3 g).

Step U: The deuterated aniline 36 (1.3 g) is diazotized by treating it with sodium nitrite (1.1 equiv) in the presence of sulfuric acid at 0° C. for 6 hours. The diazonium salt intermediate is treated with potassium cyanide (1 equiv) at 0° C. to room temperature for 6 hours. Aqueous $NaHCO_3$ solution is added to the reaction mixture slowly and then extracted with solvent mixture of ether/ethyl acetate. The combined extracts are dried over anhydrous sodium sulfate, filtered and concentrated in vacuo. The product is isolated by purification of the residue by flash column chromatography to afford the nitrile 37 (0.9 g).

Using the microwave irradiation method as described in step T, 37 (0.9 g) is converted into 38 (0.65 g) by substituting deuterium ortho to fluorine substituent at the benzene ring of 38.

38 is then converted to the corresponding aldehydes and bromide as described for 27 in Scheme 8 to couple with 21 to produce the deuterated derivatives of pyrimidines 33 and 34.

All compounds of formula I containing deuterated N-D group is prepared from the corresponding N—H containing precursor by treating N—H precursor with deuterated methanol-$d_1$ ($CH_3OD$) or methanol-$d_4$ ($CD_3OD$) or deuterated acetic acid-$d_4$ ($CD_3CO_2D$).

The pharmaceutical salts including maleate, fumarate, acetate, mesylate, tartarate, citrate, HCl, etc., are prepared by treatment of the free bases e.g., 33 and 34 with appropriate acids in a suitable solvent such as ether, methanol, or methylene chloride, followed by removal of the solvent in vacuo.

Scheme 9:

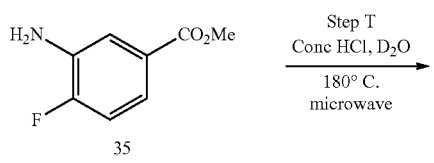

-continued

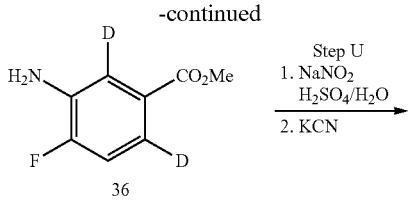

Step U
1. NaNO$_2$ H$_2$SO$_4$/H$_2$O
2. KCN

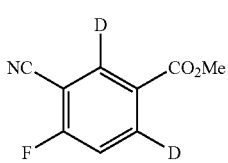

37

Step T

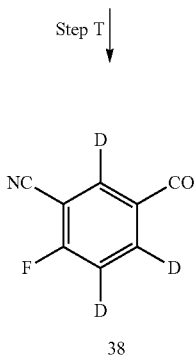

38

EXAMPLES

Given below are compounds that are representative examples of the present invention.

Example 1

N-(1-(3-Cyano-4-fluorobenzyl-d$_2$)piperidin-4-yl-d$_5$)-6-chlorothieno-d$_1$[2,3-d]pyrimidine-4-amine-d$_1$

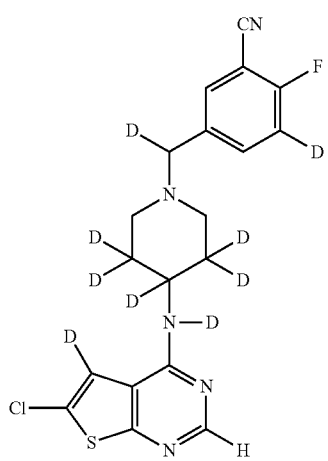

The title compound is prepared by using the methods described in scheme above. Mass spectral analysis (m/e): 411 (M+1).

Example 2

N-(1-(3-Cyano-4-fluorobenzyl-d$_4$)piperidin-4-yl-d$_5$)-6-chlorothieno-d$_1$[2,3-d]pyrimidine-4-amine-d$_1$

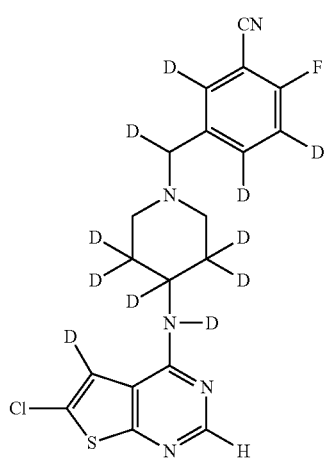

The title compound is prepared by using the methods described in scheme above. MS (m/e): 413 (M+1).

Example 3

N-(1-(3-Cyano-4-fluorobenzyl-d$_5$)piperidin-4-yl-d$_5$)-6-chlorothieno-d$_1$[2,3-d]pyrimidine-4-amine-d$_1$

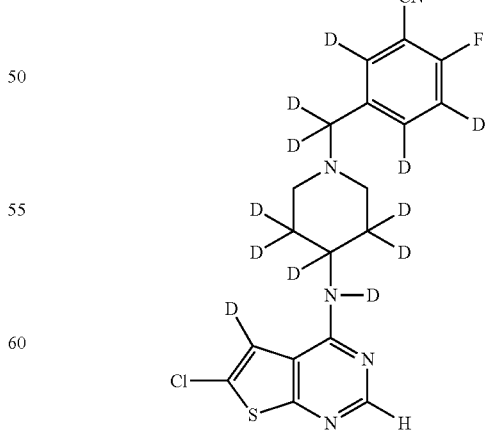

The title compound is prepared by using the methods described in scheme above. MS (m/e): 414 (M+1).

Example 4

N-(1-(3-Cyano-4-fluorobenzyl-d$_5$)piperidin-4-yl-d$_5$)-6-chlorothieno-d$_1$[2,3-d]pyrimidine-d$_1$-4-amine-d$_1$

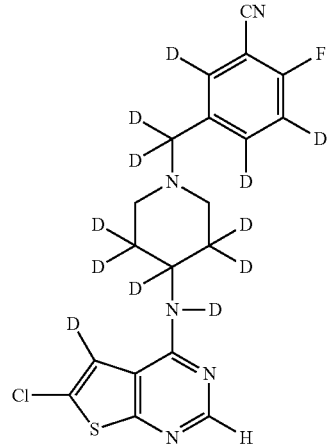

The title compound is prepared by using the methods described in schemes above. MS (m/e): 415 (M+1).

Example 5

N-(1-(3-Cyano-4-fluorobenzyl-d$_2$)piperidin-4-yl-d$_5$)-6-chlorothieno-d$_1$[3,2-d]pyrimidine-4-amine-d$_1$

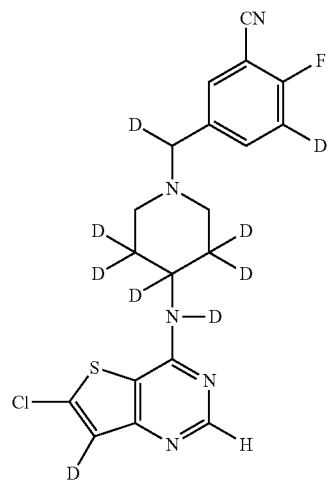

The title compound is prepared by using the methods described in scheme above. Mass spectral analysis (m/e): 411 (M+1).

Example 6

N-(1-(3-Cyano-4-fluorobenzyl-d$_4$)piperidin-4-yl-d$_5$)-6-chlorothieno-d$_1$[3,2-d]pyrimidine-4-amine-d$_1$

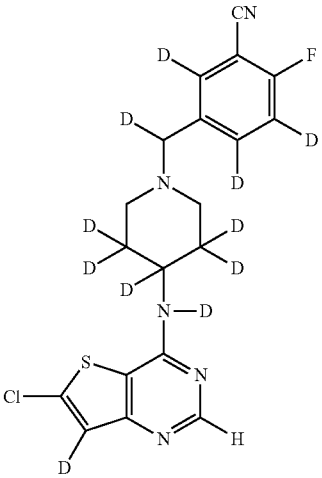

The title compound is prepared by using the methods described in scheme above. MS (m/e): 413 (M+1).

Example 7

N-(1-(3-Cyano-4-fluorobenzyl-d$_5$)piperidin-4-yl-d$_5$)-6-chlorothieno-d$_1$[3,2-d]pyrimidine-4-amine-d$_1$

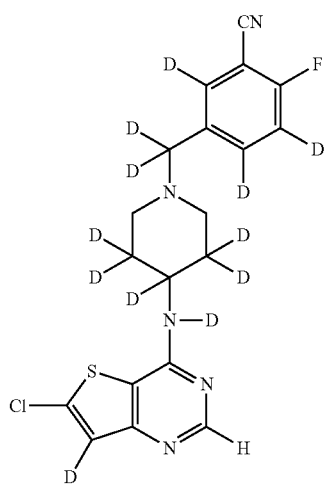

The title compound is prepared by using the methods described in scheme above. MS (m/e): 414 (M+1).

Example 8

N-(1-(3-Cyano-4-fluorobenzyl-$d_5$)piperidin-4-yl-$d_5$)-6-chlorothieno-$d_1$[3,2-d]pyrimidine-$d_1$-4-amine-$d_1$

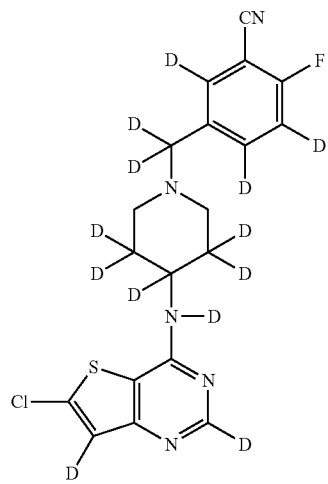

The title compound is prepared by using the methods described in scheme above. MS (m/e): 415 (M+1).

Example 9

N-(1-(3-Cyano-4-fluorobenzyl-$d_2$)piperidin-4-yl-$d_5$)-2-chlorothiazolo[5,4-d]pyrimidine-7-amine-$d_1$

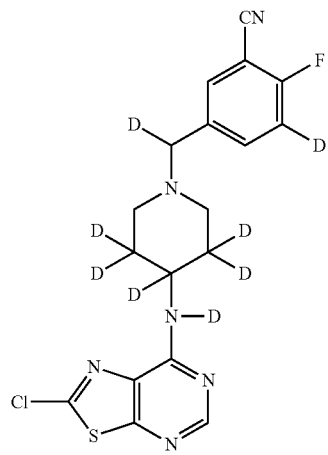

The title compound is prepared by using the methods described in scheme above. MS (m/e): 411 (M+1).

Example 10

N-(1-(3-Cyano-4-fluorobenzyl-$d_4$)piperidin-4-yl-$d_5$)-2-chlorothiazolo[5,4-d]pyrimidine-7-amine-$d_1$

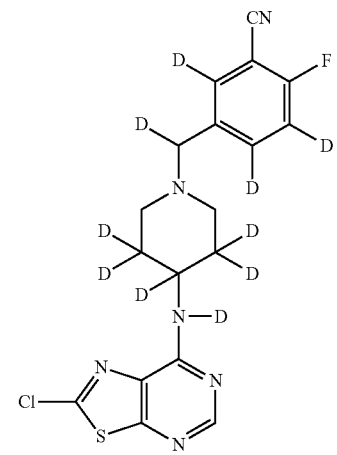

The title compound is prepared by using the methods described in scheme above. MS (m/e): 413 (M+1).

Example 11

N-(1-(3-Cyano-4-fluorobenzyl-$d_5$)piperidin-4-yl-$d_5$)-2-chlorothiazolo[5,4-d]pyrimidine-7-amine-$d_1$ The title compound is prepared by using the methods described in scheme above. MS (m/e): 414 (M+1).

Example 12

N-(1-(3-Cyano-4-fluorobenzyl-$d_5$)piperidin-4-yl-$d_5$)-2-chlorothiazolo[5,4-d]pyrimidine-5-$d_1$-7-amine-$d_1$

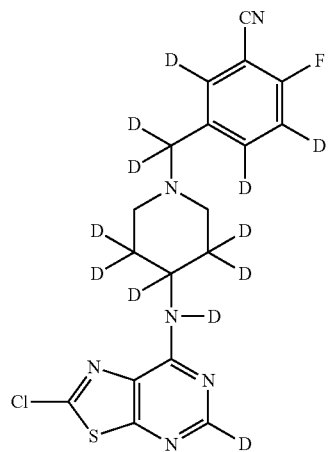

The title compound is prepared by using the methods described in scheme above. MS (m/e): 415 (M+1).

Example 13

N-(1-(3-Cyano-4-fluorobenzyl-$d_2$)piperidin-4-yl-$d_5$)-2-chlorothiazolo[4,5-d]pyrimidine-7-amine-$d_1$

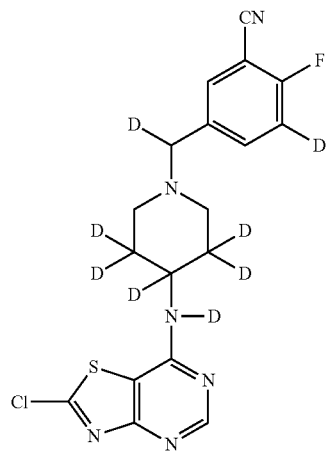

The title compound is prepared by using the methods described in scheme above. MS (m/e): 411 (M+1).

Example 14

N-(1-(3-Cyano-4-fluorobenzyl-$d_4$)piperidin-4-yl-$d_5$)-2-chlorothiazolo[4,5-d]pyrimidine-7-amine-$d_1$

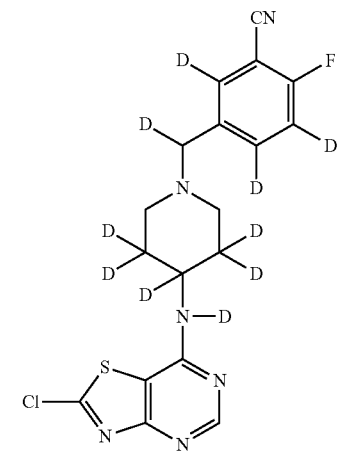

The title compound is prepared by using the methods described in scheme above. MS (m/e): 413 (M+1).

Example 15

N-(1-(3-Cyano-4-fluorobenzyl-$d_5$)piperidin-4-yl-$d_5$)-2-chlorothiazolo[4,5-d]pyrimidine-7-amine-$d_1$

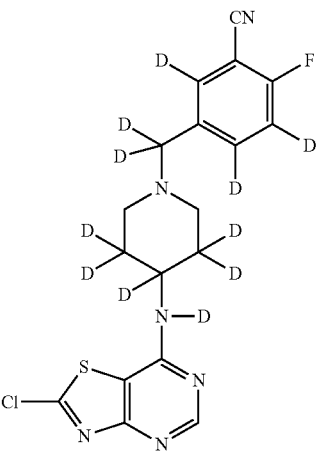

The title compound is prepared by using the methods described in scheme above. MS (m/e): 414 (M+1).

Example 16
N-(1-(3-Cyano-4-fluorobenzyl-$d_5$)piperidin-4-yl-$d_5$)-2-chlorothiazolo[4,5-d]pyrimidine-5-$d_1$-7-amine-$d_1$
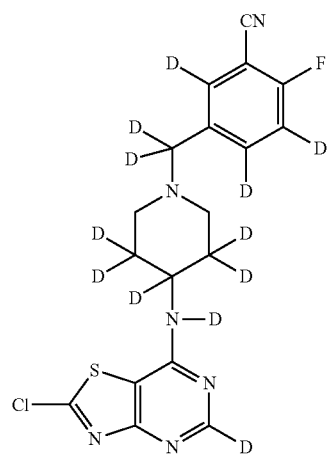
The title compound is prepared by using the methods described in scheme above. MS (m/e): 415 (M+1).
17
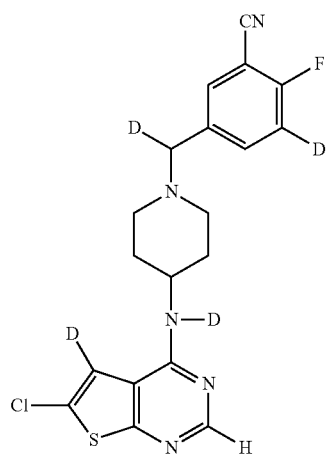
18
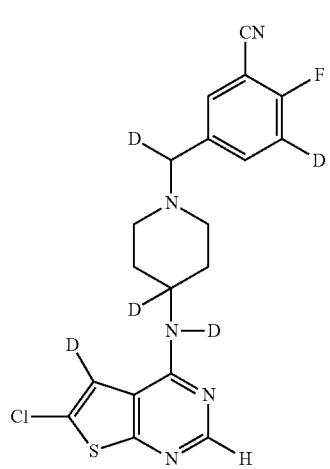
19
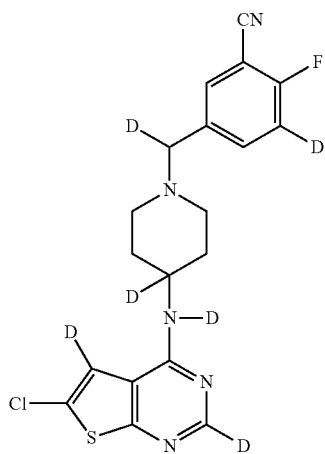
20
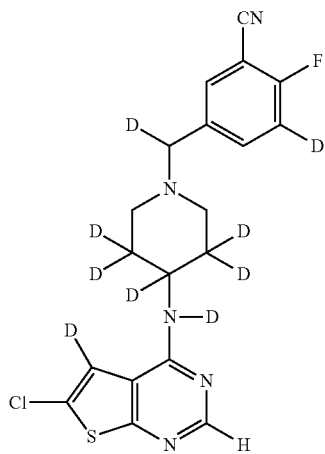
21
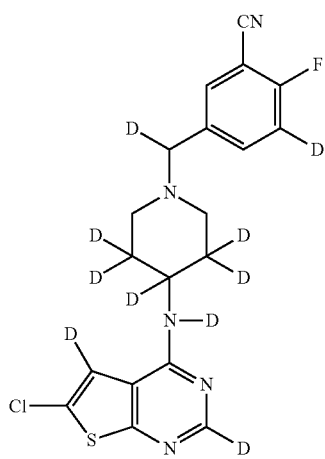

22
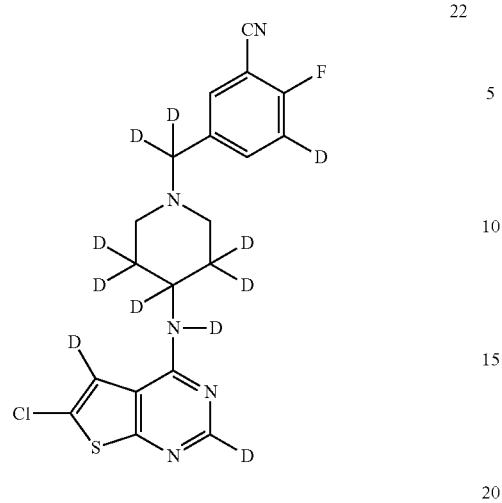
23
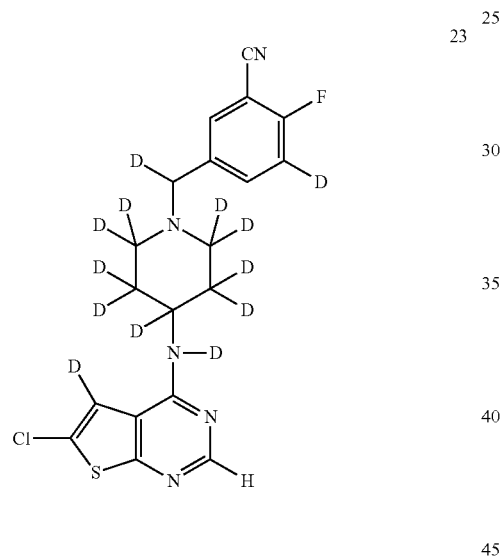
24
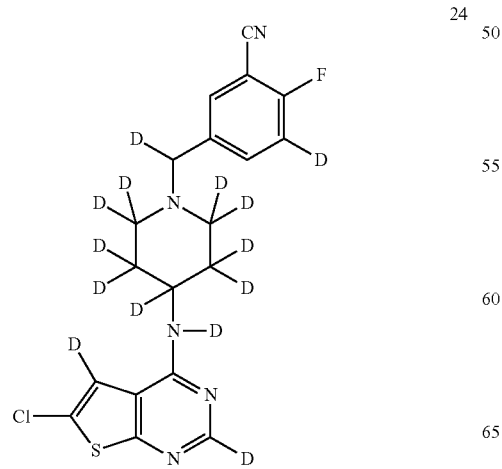
25
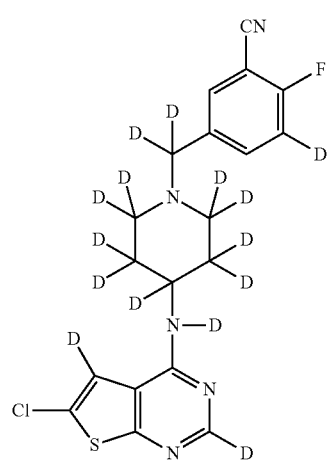
26
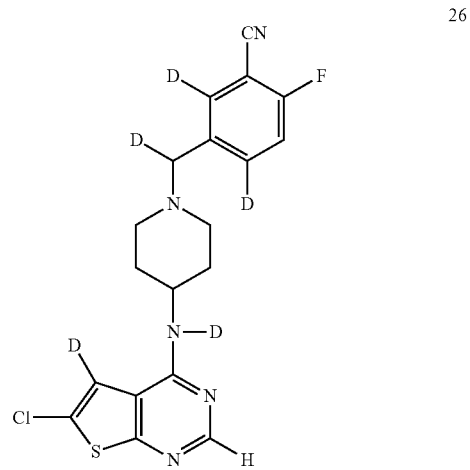
27
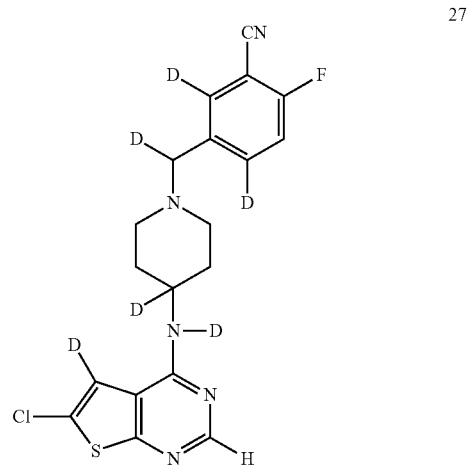

| 28 | 31 |
|---|---|
| 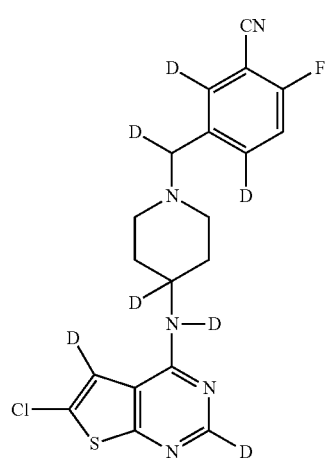 | 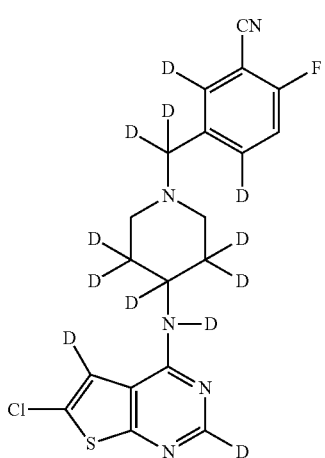 |
| 29 | 32 |
| 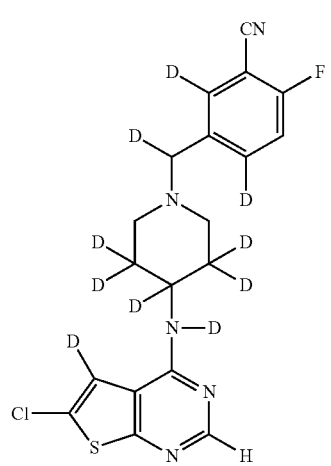 | 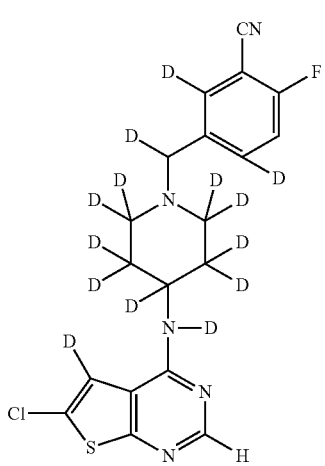 |
| 30 | 33 |
| 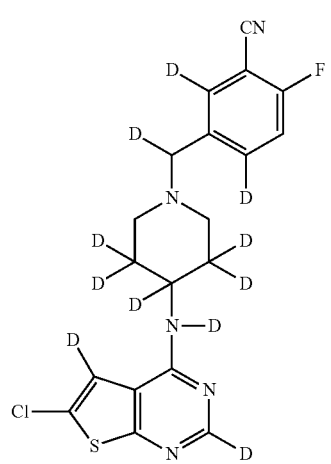 | 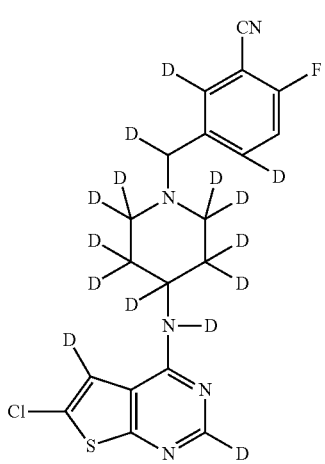 |

-continued
34
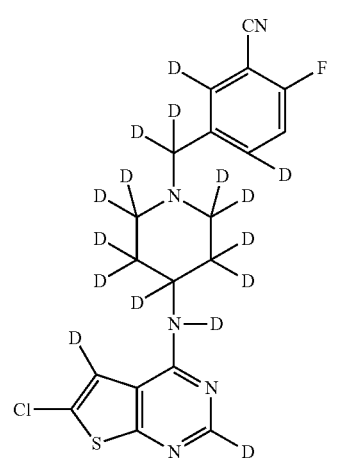
35
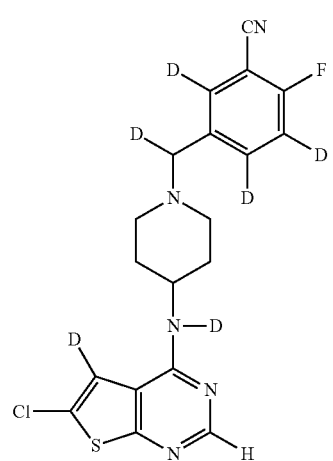
36
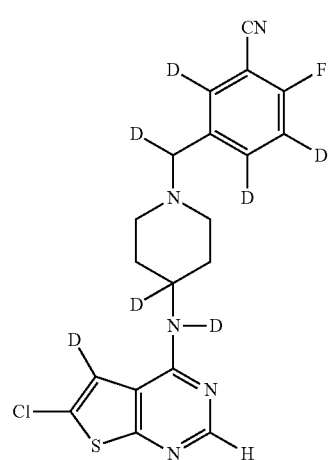
-continued
37
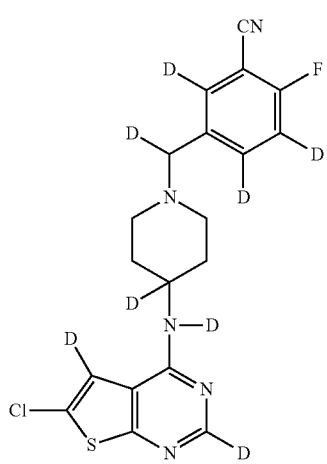
38
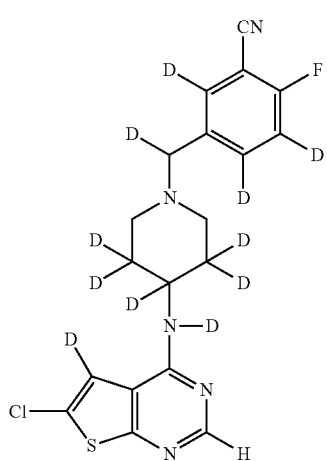
39
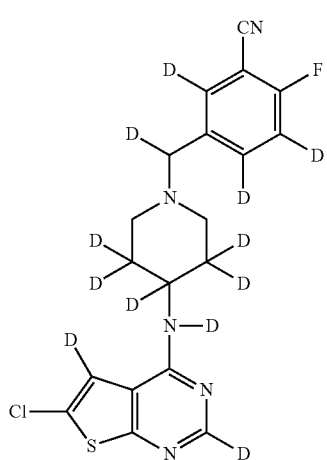

40
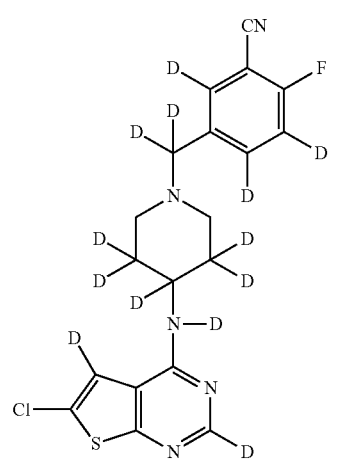
41
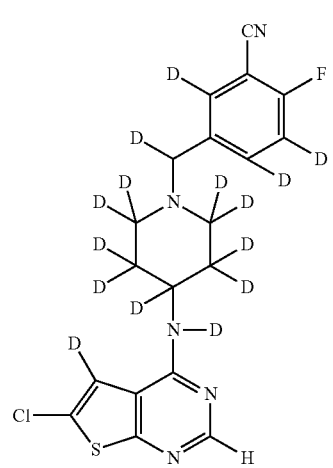
42
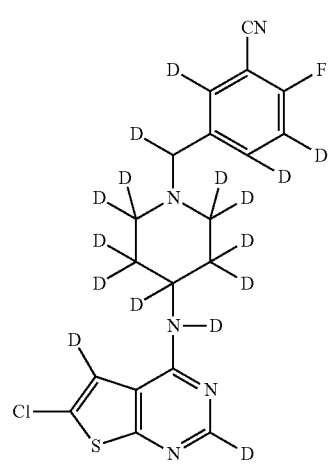
42
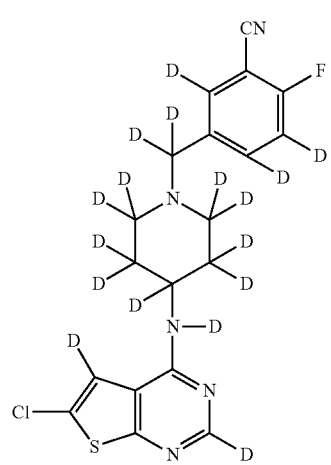
43
44
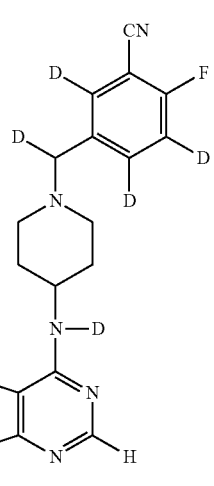
45
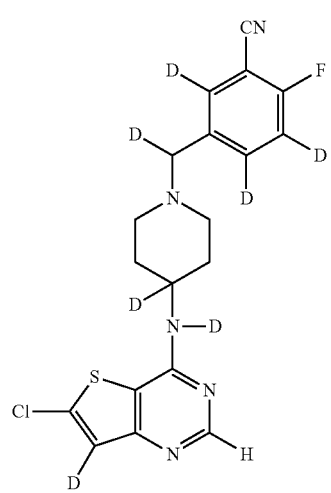

46
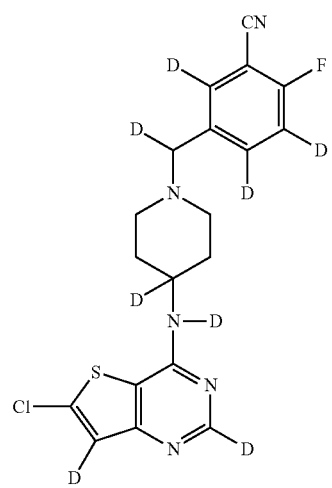
47
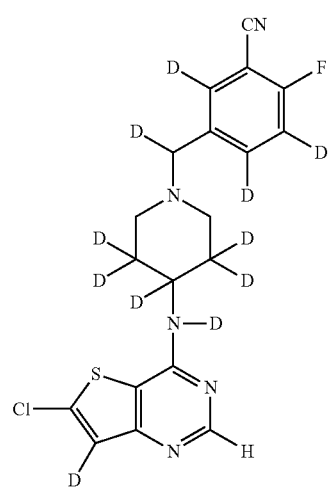
48
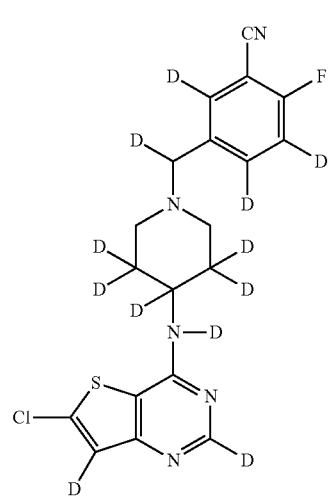
49
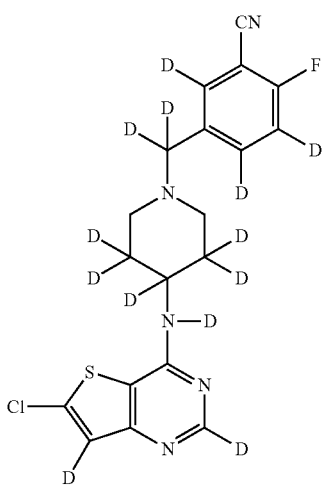
50
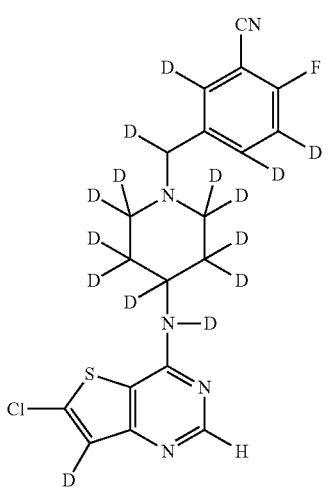
51
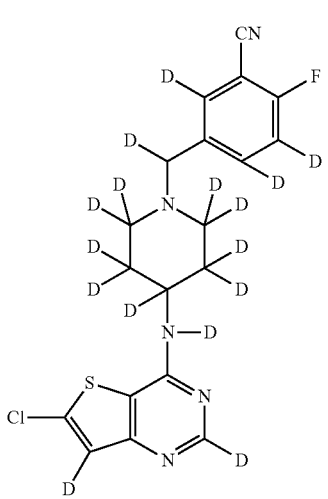

52 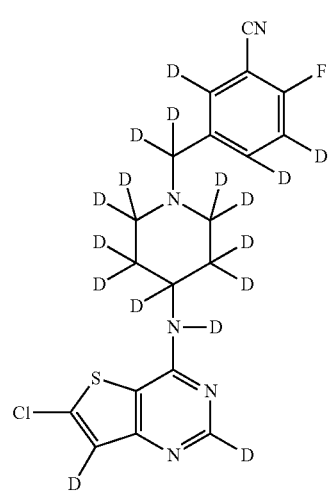
53 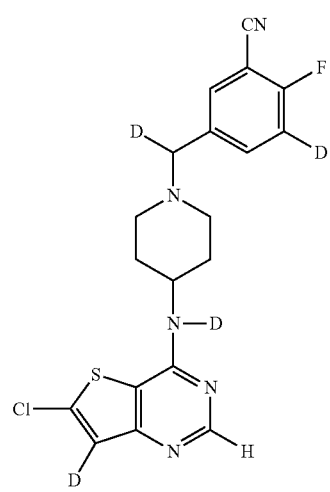
54 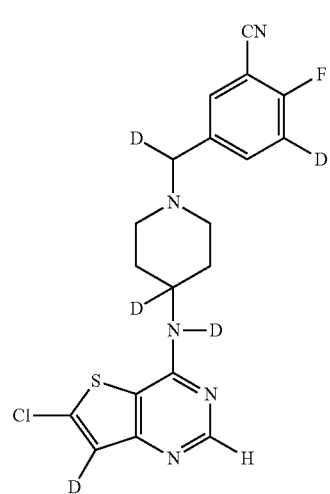
55 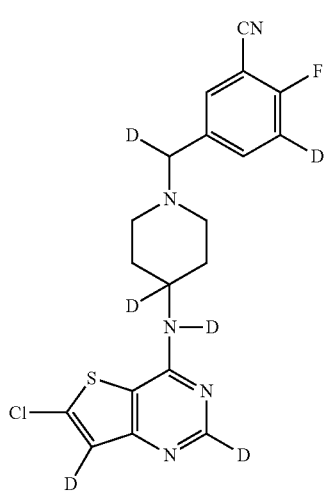
56 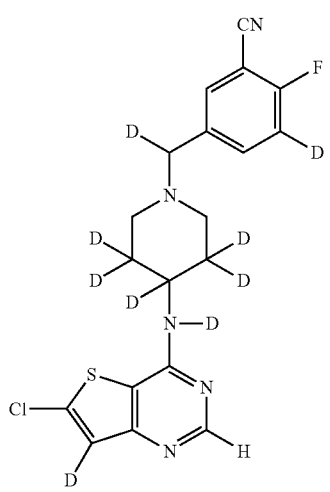
57 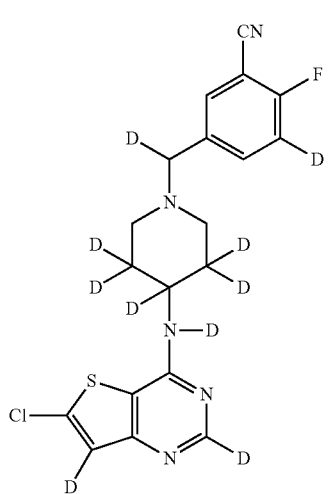

58
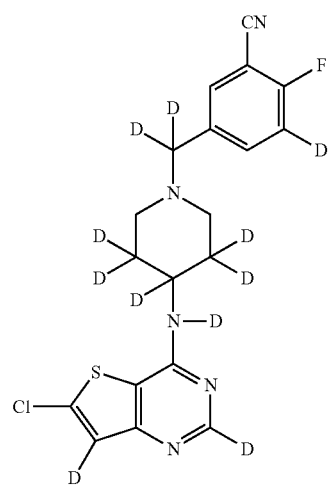
59
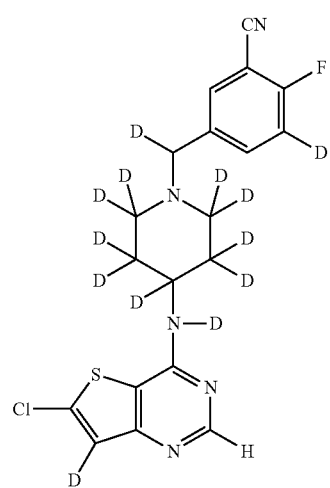
60
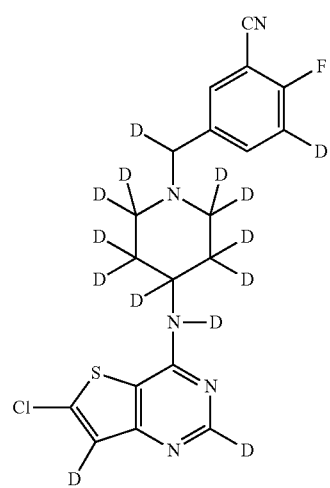
61
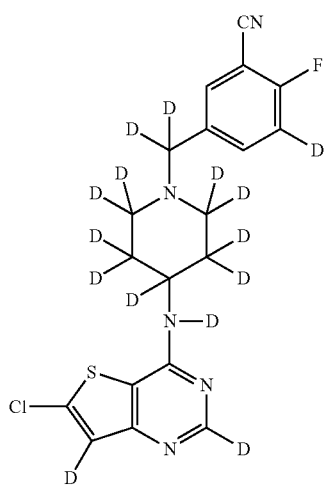
62
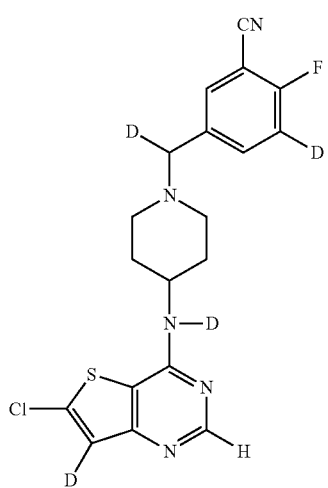
63
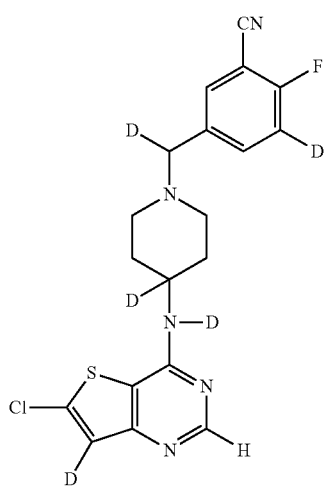

64
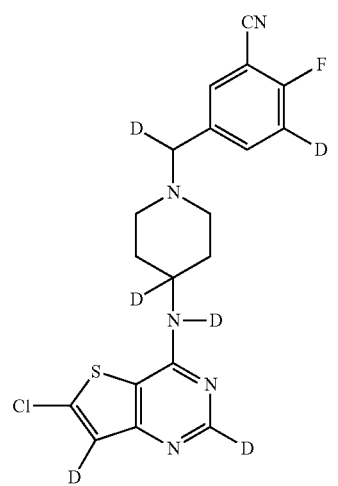
65
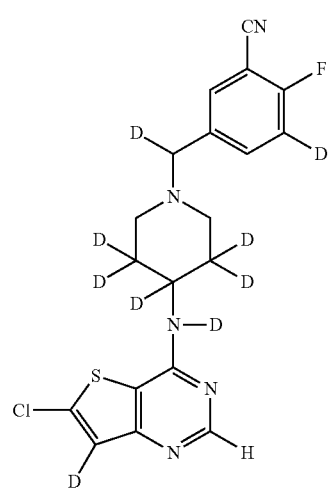
66
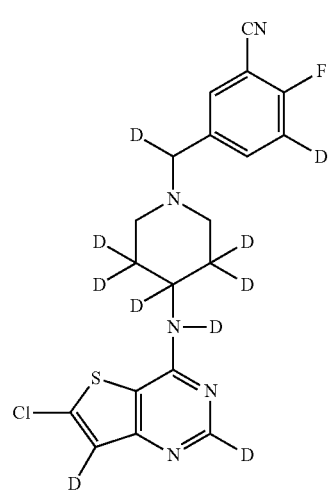
67
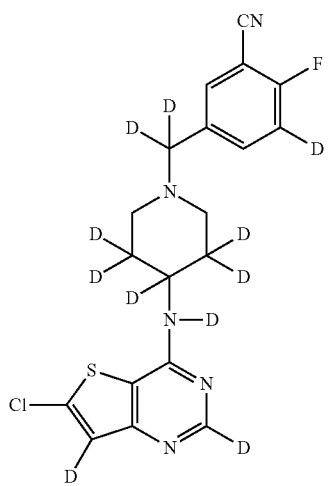
68
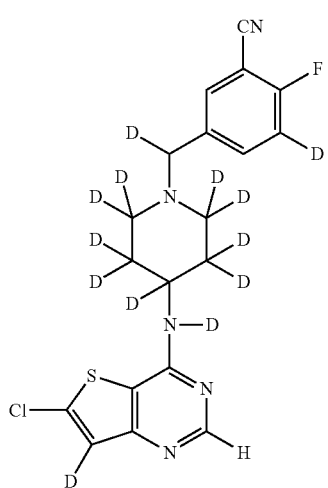
69
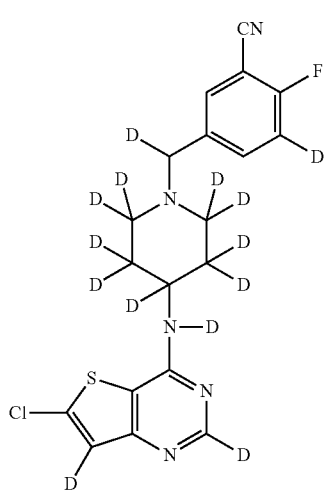

70
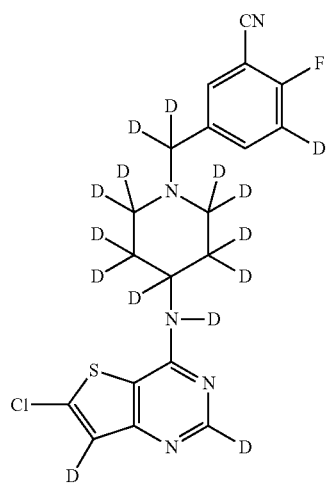
71
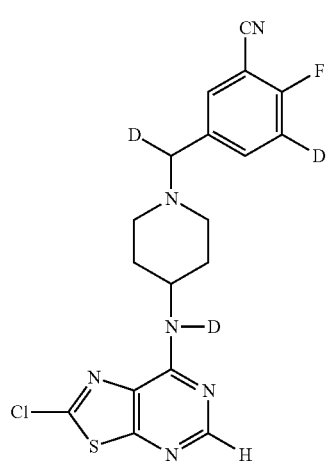
72
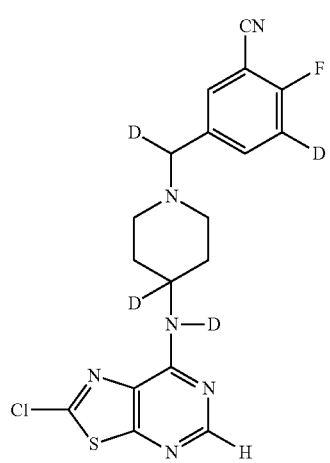
73
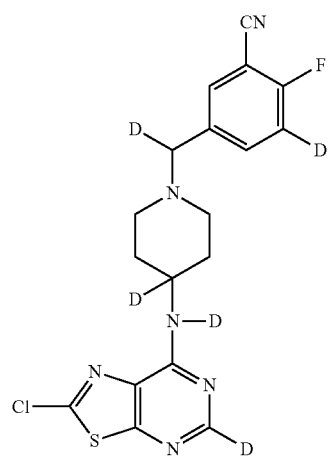
74
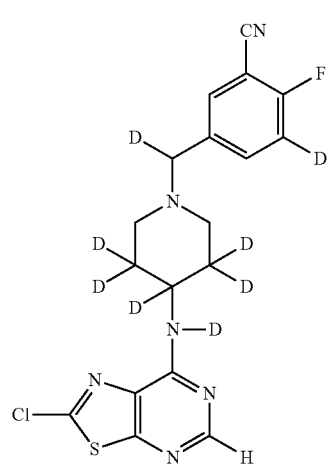
75
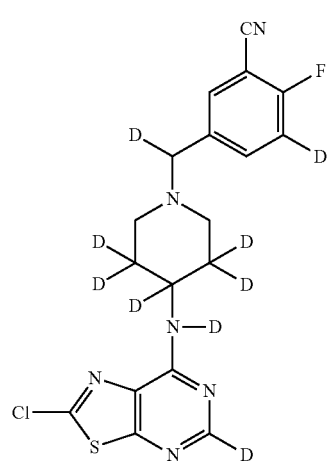

76

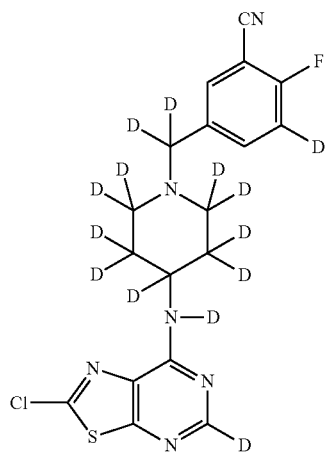

77

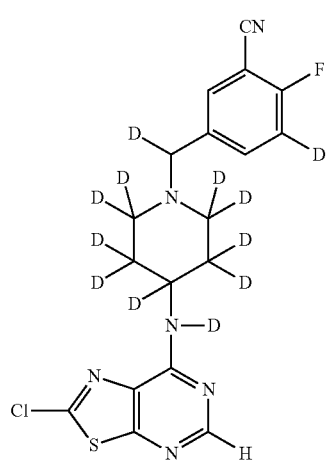

78

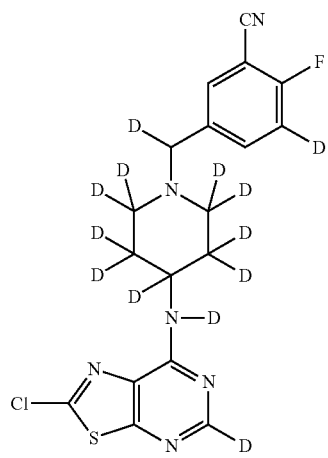

79

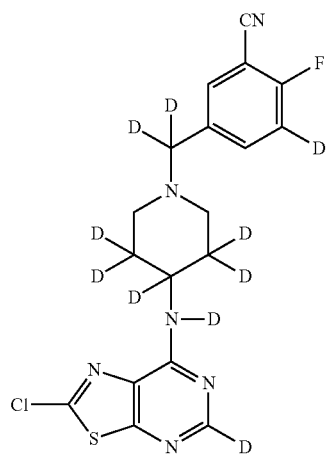

Those skilled in the art will recognize or be able to ascertain using no more than routine experimentation, numerous equivalents to the specific reagents can be utilized to produce compounds of the invention. Numerous modifications and variations of the present invention are possible and therefore it is understood that within the scope of the appended claims, the invention may be practiced otherwise that as specifically described herein. Other aspects, advantages and modifications are within the scope of the invention.

What is claimed is:

1. A method of treating a disease selected from the group consisting of carcinoid syndrome, neuroendocrine neoplasia tumor progression, neuroendocrine neoplasia tumor fibrosis and neuroendocrine neoplasia tumor metastasis comprising administering a pharmaceutically acceptable dose of a deuterium-enriched compound of formula 1, or a pharmaceutically acceptable salt thereof,

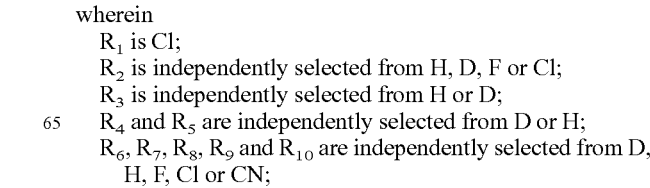

wherein
$R_1$ is Cl;
$R_2$ is independently selected from H, D, F or Cl;
$R_3$ is independently selected from H or D;
$R_4$ and $R_5$ are independently selected from D or H;
$R_6$, $R_7$, $R_8$, $R_9$ and $R_{10}$ are independently selected from D, H, F, Cl or CN;

$R_{11}$, $R_{12}$, $R_{13}$, $R_{14}$, $R_{15}$, $R_{16}$, $R_{17}$, $R_{18}$, and $R_{19}$ are independently selected from D or H;

$R_{20}$ is selected from D or H and at least one of $R_2$, $R_5$, $R_9$, $R_{11}$, $R_{17}$, and $R_{18}$ is D, to a patient in need of such treatment.

2. The method of claim 1 wherein the disease is neuoroendocrine neoplasia tumor progression, neuoroendocrine neoplasia tumor fibrosis and neuoroendocrine neoplasia tumor metastasis.

3. The method of claim 1 wherein the disease is carcinoid syndrome.

4. The method of claim 1 wherein the compound is selected from the group consisting of

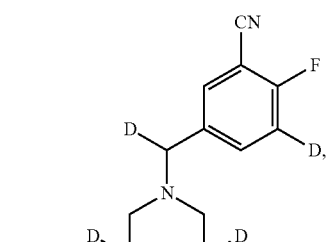
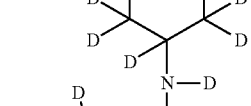
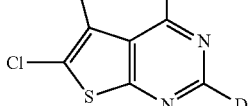
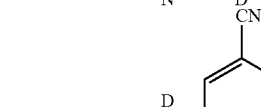
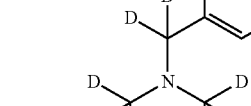
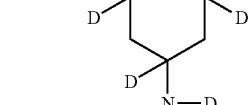
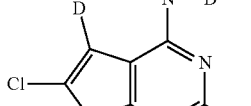
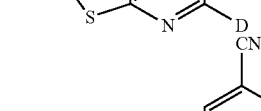
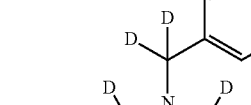
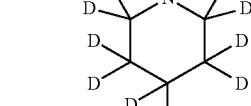
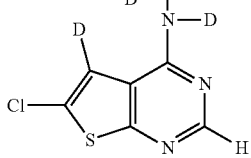

-continued

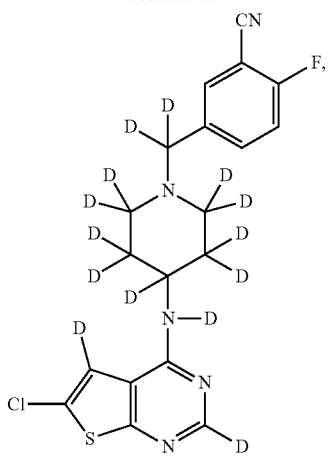

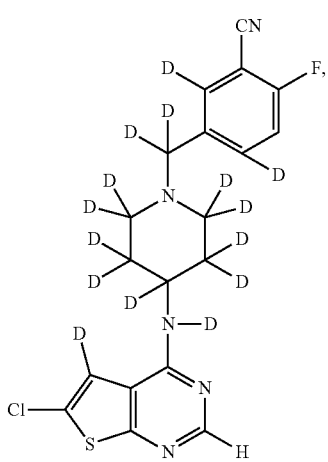

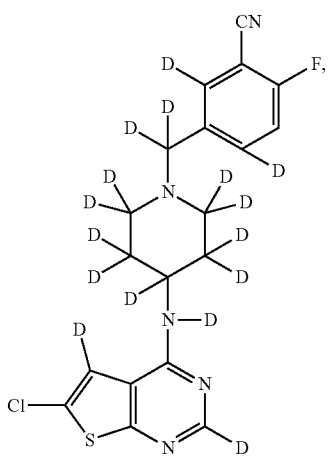

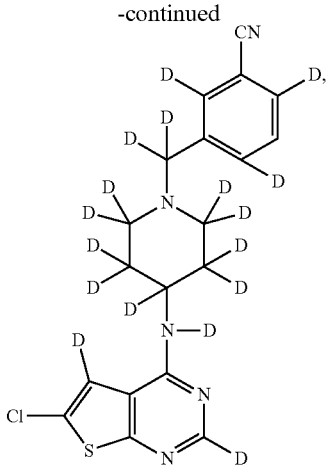
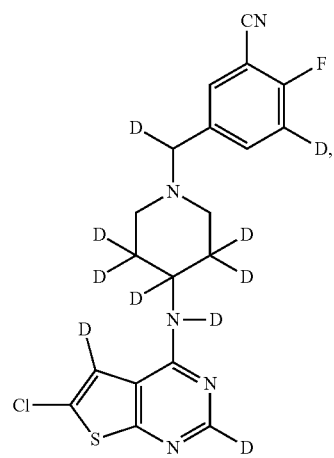
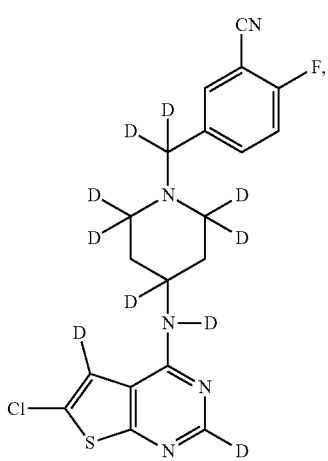
and
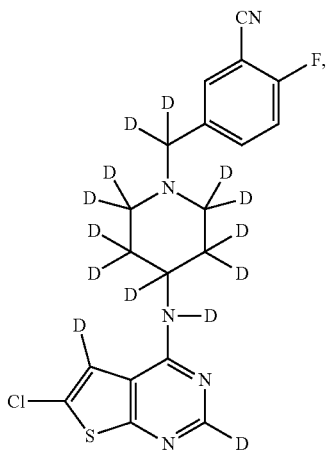
5. The method of claim 4 wherein the compound is selected from the group consisting of -continued

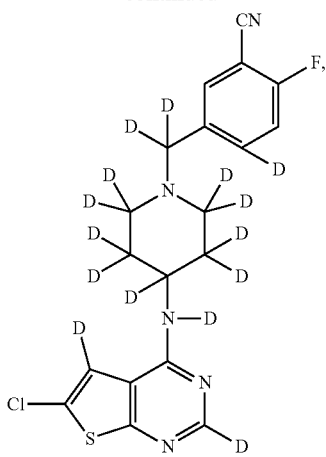

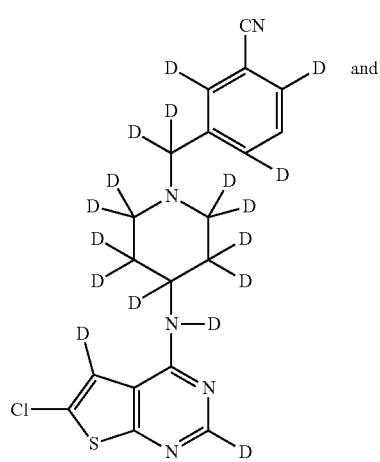

and

6. A method of treating neuoroendocrine neoplasia tumor fibrosis comprising administering a pharmaceutically acceptable dose of a deuterium-enriched compound of formula 1, or a pharmaceutically acceptable salt thereof,

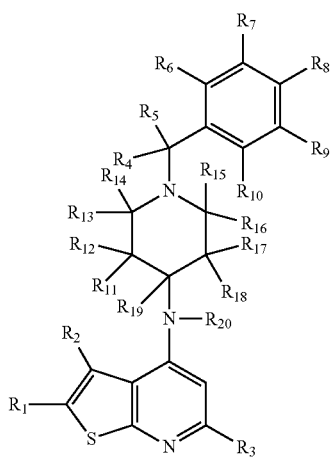

1 wherein
R$_1$ is Cl;
R$_2$ is independently selected from H, D, F or Cl;
R$_3$ is independently selected from H or D;
R$_4$ and R$_5$ are independently selected from D or H;
R$_6$, R$_7$, R$_8$, R$_9$ and R$_{10}$ are independently selected from D, H, F, Cl or CN;
R$_{11}$, R$_{12}$, R$_{13}$, R$_{14}$, R$_{15}$, R$_{16}$, R$_{17}$, R$_{18}$, and R$_{19}$ are independently selected from D or H;
R$_{20}$ is selected from D or H and
at least one of R$_2$, R$_5$, R$_9$, R$_{11}$, R$_{17}$, and R$_{18}$ is D,
to a patient in need of such treatment.

7. The method of claim 6 wherein the neuroendocrine cell disregulation is Crohn's disease.

8. The method of claim 6 wherein the compound is selected from the group consisting of

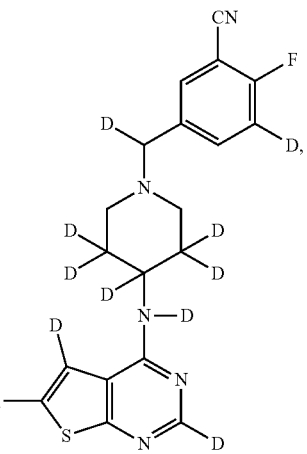

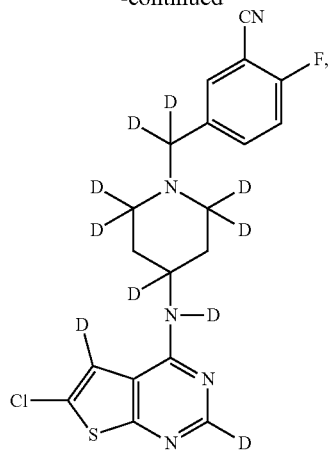
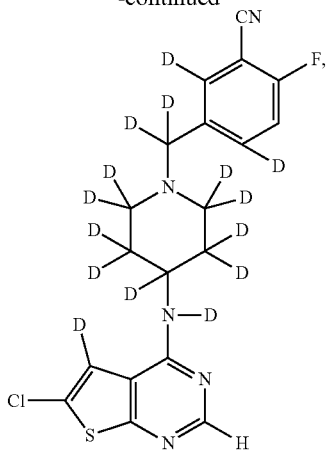
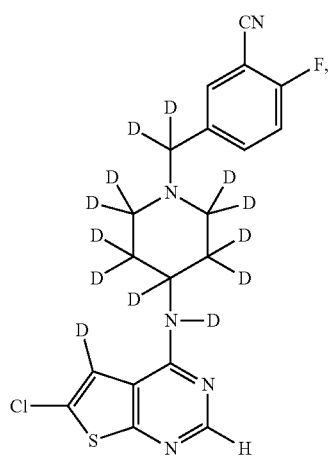
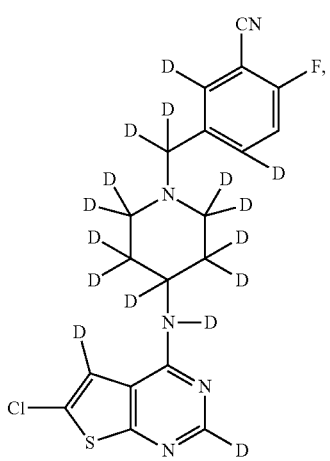
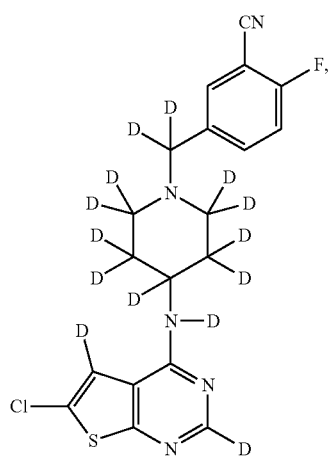
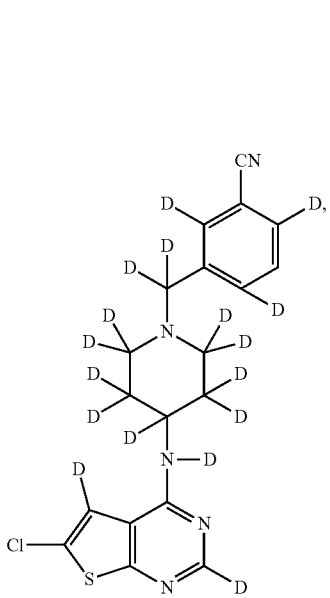

-continued
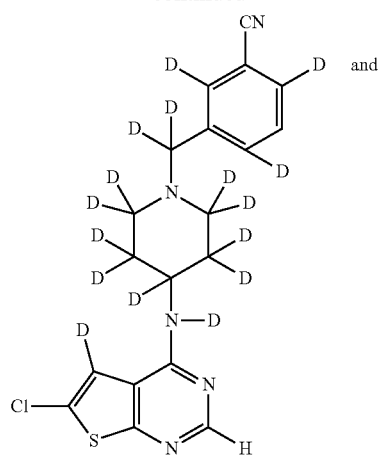
and
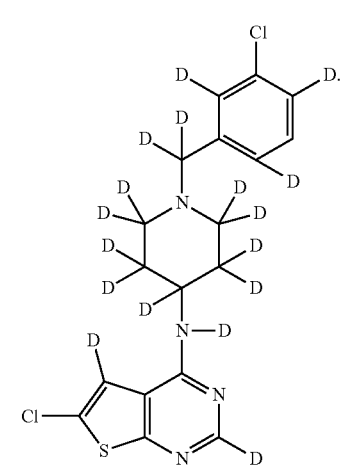
9. The method of claim 8 wherein the compound is selected from the group consisting of
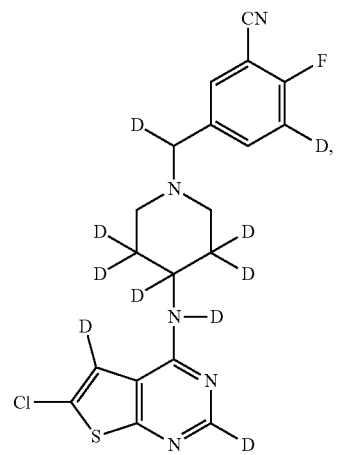
-continued
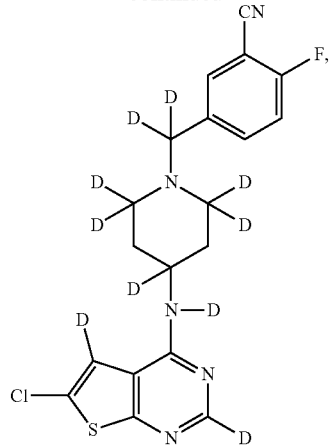
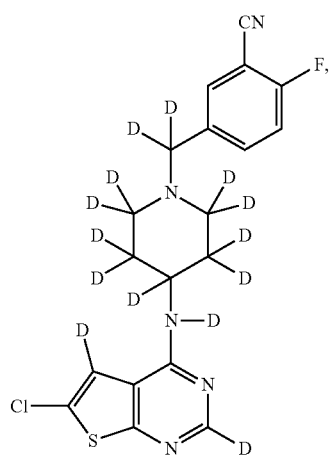

-continued

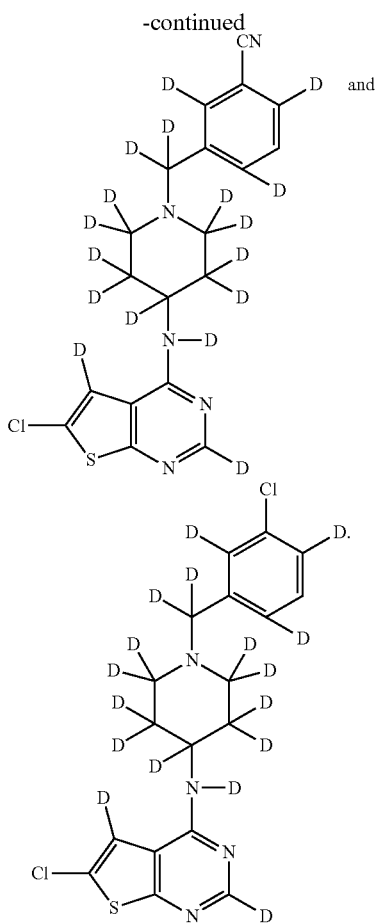

10. A method of treating a disease or condition selected from the group consisting of pulmonary arterial hypertension, pulmonary hypertension associated with COPD, right ventricular hypertrophy, portal hypertension, hypertension, -anxiety, depression, social phobia and panic disorder comprising administering a pharmaceutically acceptable dose of a deuterium-enriched compound of formula 1, or a pharmaceutically acceptable salt thereof,

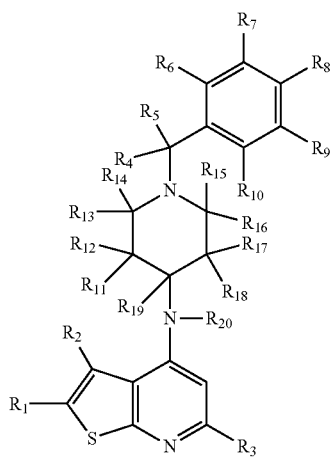

wherein
R₁ is Cl;
R₂ is independently selected from H, D, F or Cl;
R₃ is independently selected from H or D;

R₄ and R₅ are independently selected from D or H;
R₆, R₇, R₈, R₉ and R₁₀ are independently selected from D, H, F, Cl or CN;
R₁₁, R₁₂, R₁₃, R₁₄, R₁₅, R₁₆, R₁₇, R₁₈, and R₁₉ are independently selected from D or H;
R₂₀ is selected from D or H H
to a patient in need of such treatment, and
at least one of R₂, R₅, R₉, R₁₁, R₁₇, and R₁₈ is D.

11. The method of claim 10 wherein the disease is selected from the group consisting of hypertension, pulmonary arterial hypertension, pulmonary hypertension associated with COPD, right ventricular hypertrophy, and portal hypertension.

12. The method of claim 10 wherein the disease or disorder is selected from the group consisting of anxiety, depression, social phobia and panic disorder.

13. The method of claim 10 wherein the compound is selected from the group consisting of

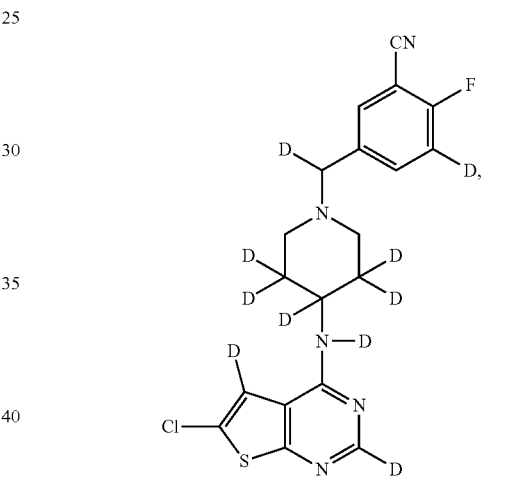

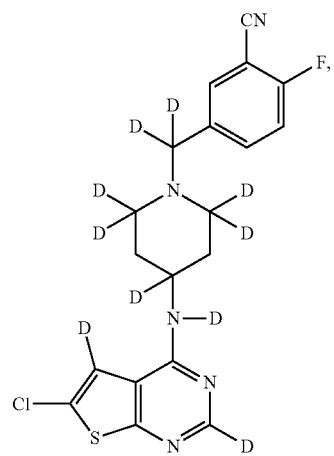

-continued
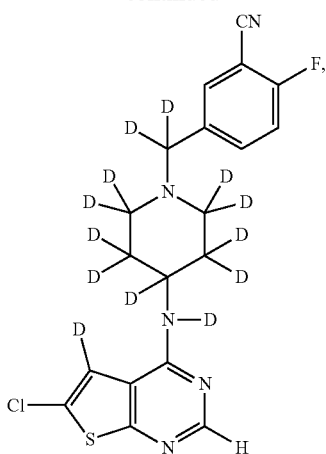
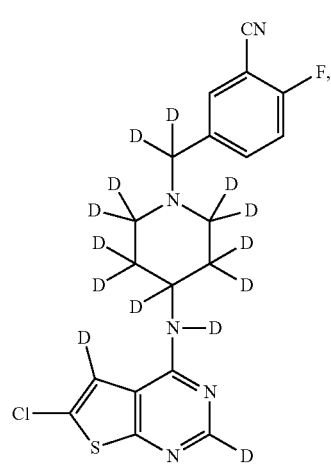
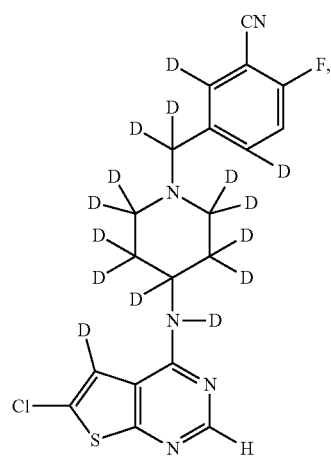
-continued
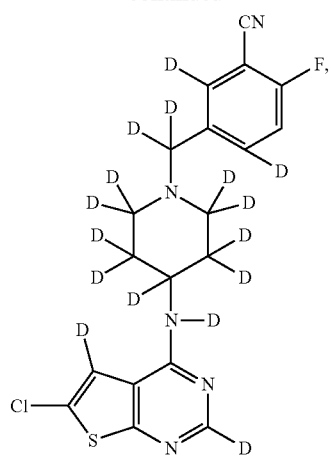
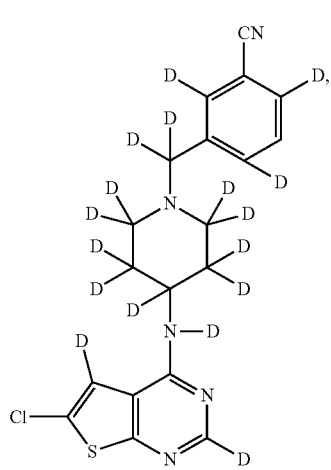
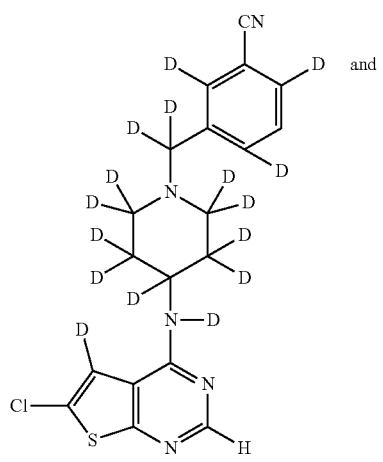
and -continued
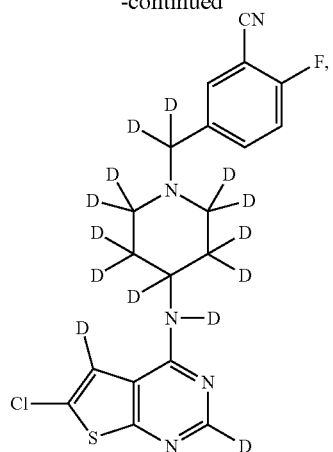
14. The method of claim 10 wherein the compound is selected from the group consisting of
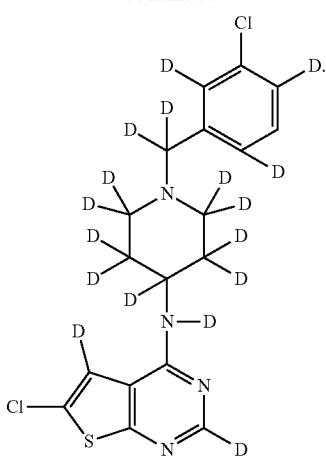
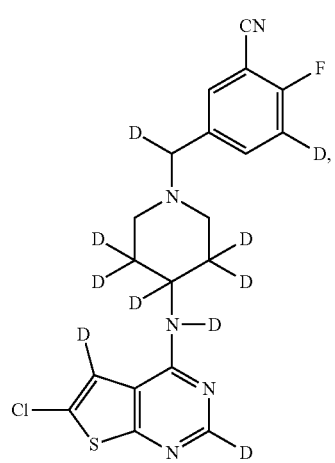
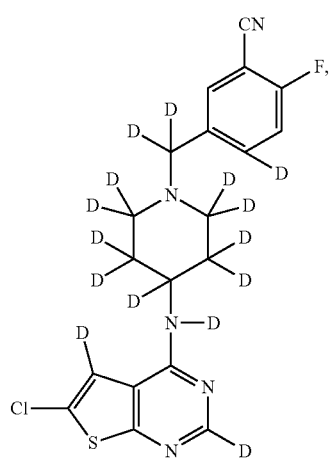
and
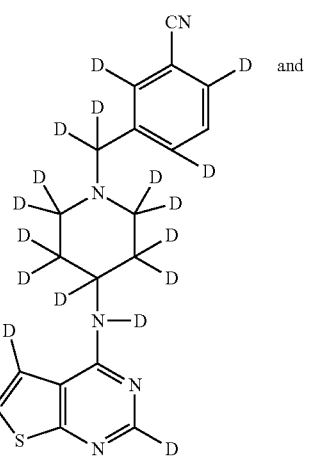

-continued
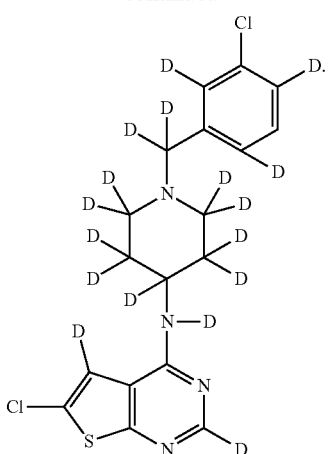
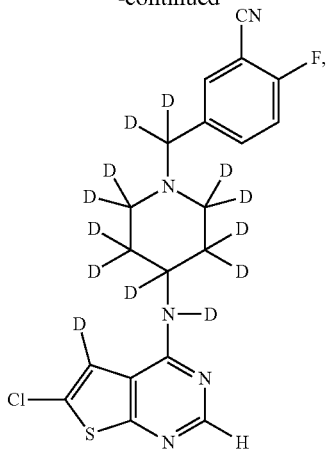
15. The method of claim 2 wherein the compound is selected from the group consisting of
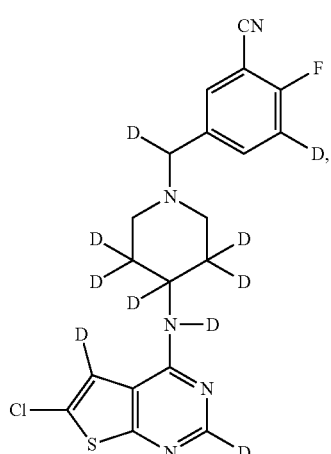
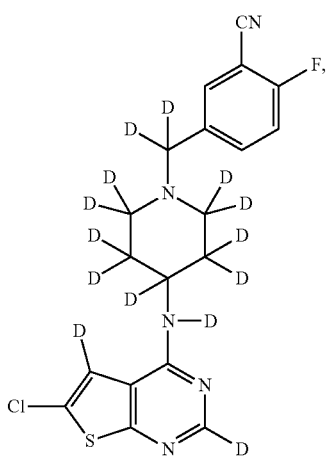
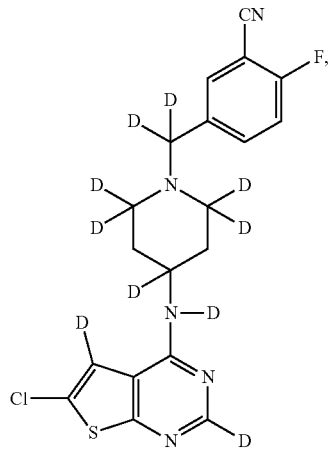
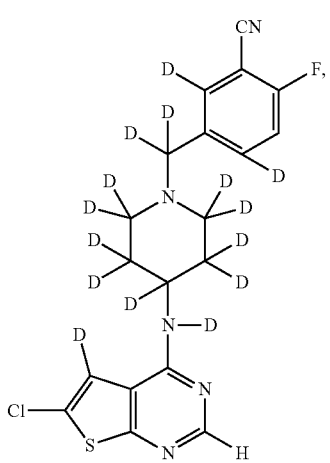

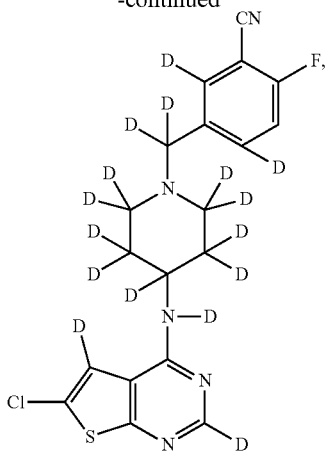
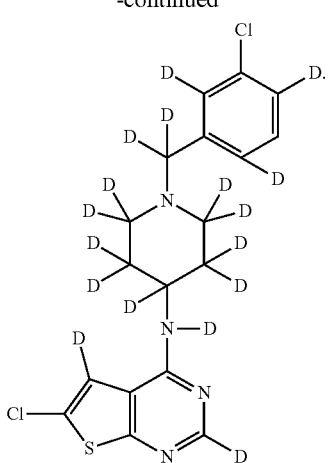
16. The method of claim 15 wherein the compound is selected from the group consisting of -continued
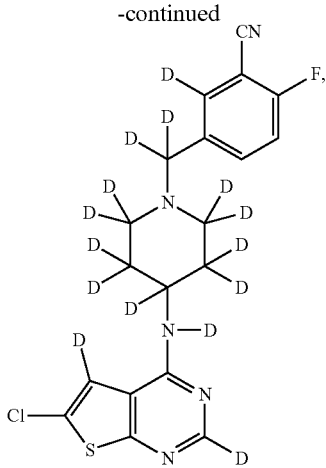
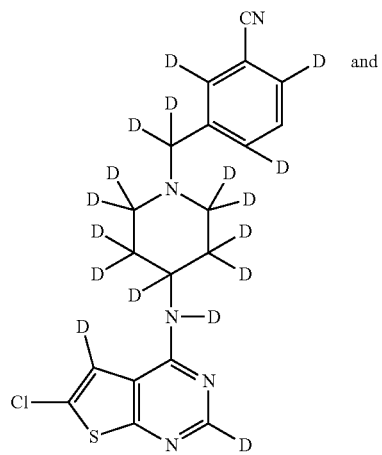
-continued
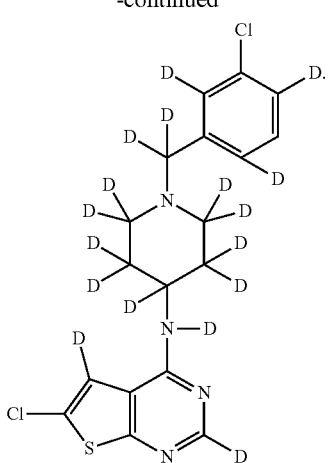
17. The method of claim 3 wherein the compound is selected from the group consisting of
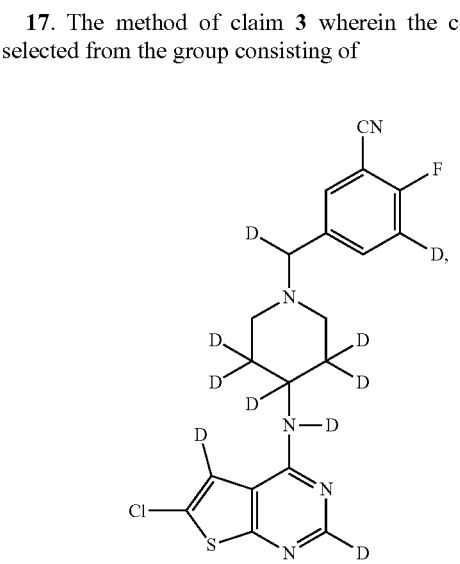
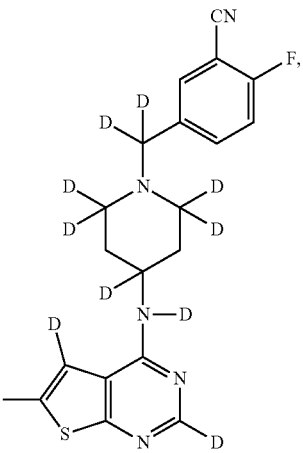

77
-continued
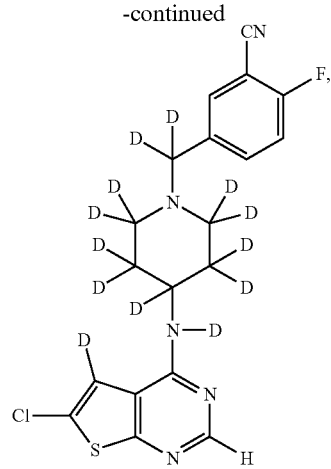
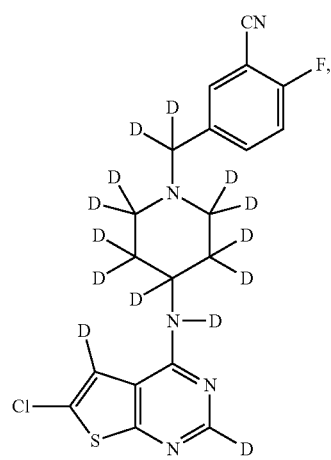
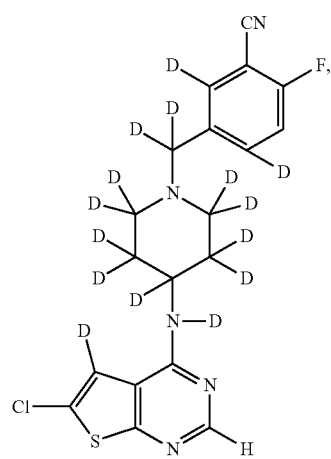
78
-continued
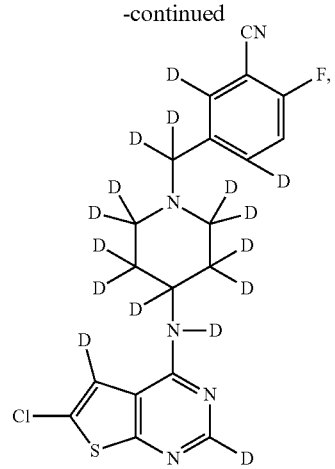
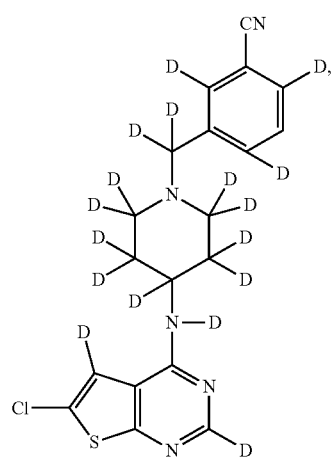
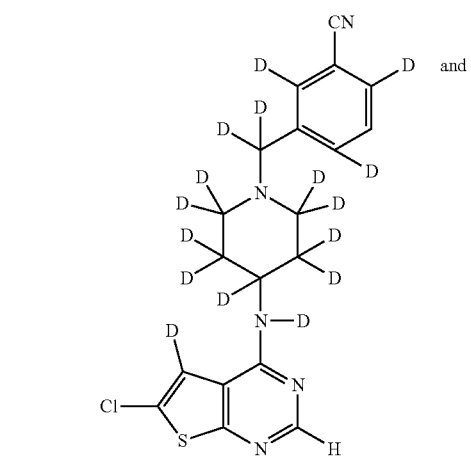
and -continued
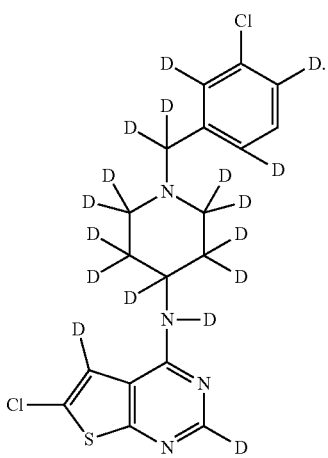
18. The method of claim 17 wherein the compound is selected from the group consisting of
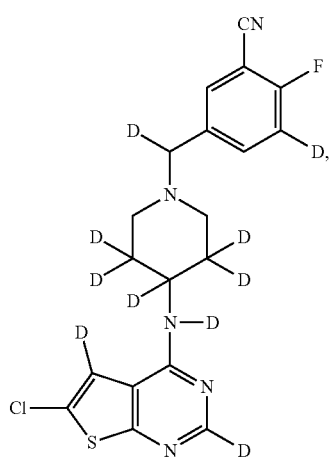
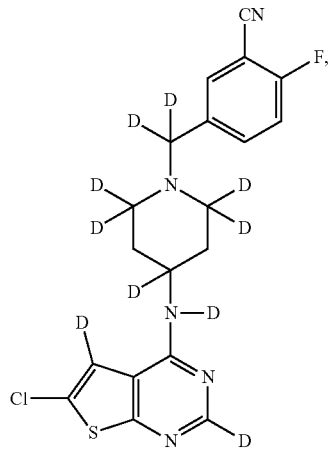
-continued
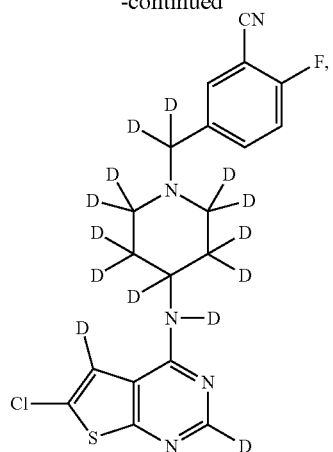
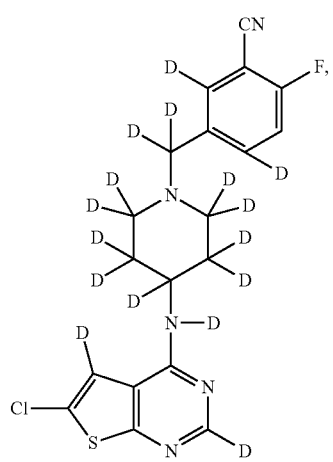
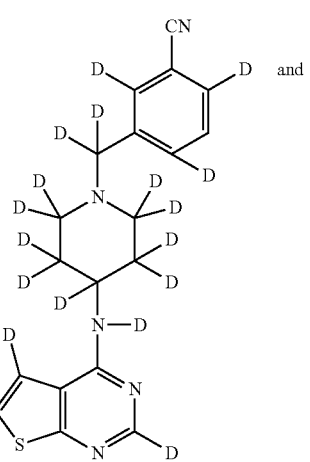 and -continued
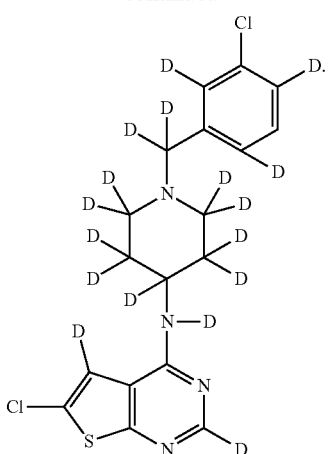
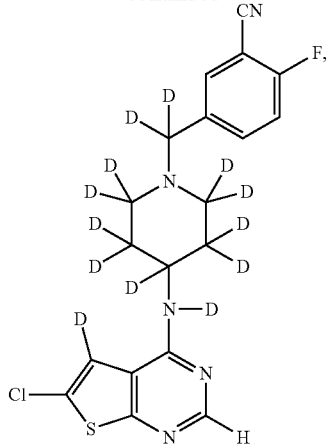
19. The method of claim 6 wherein the compound is selected from the group consisting of
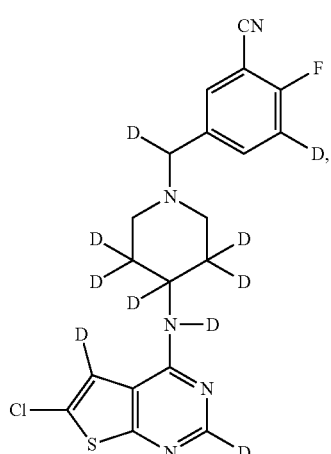
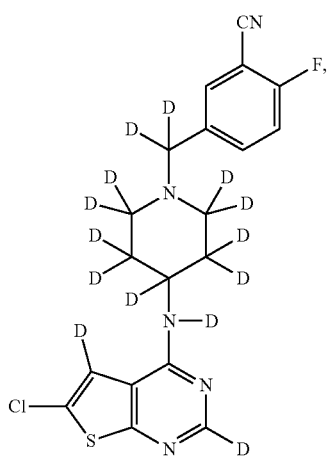
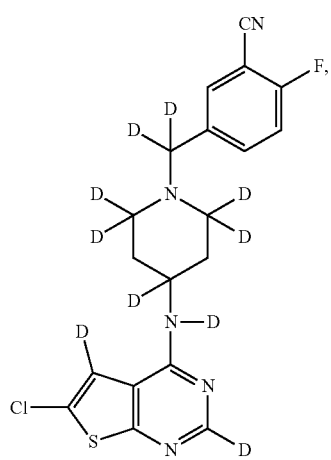
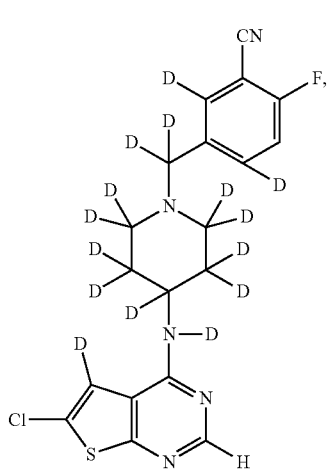

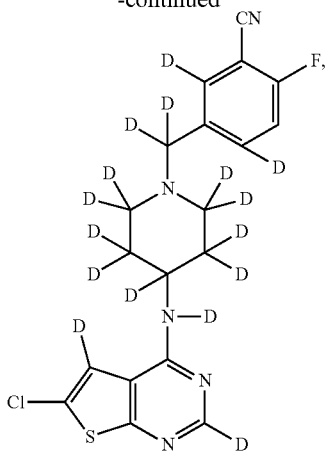
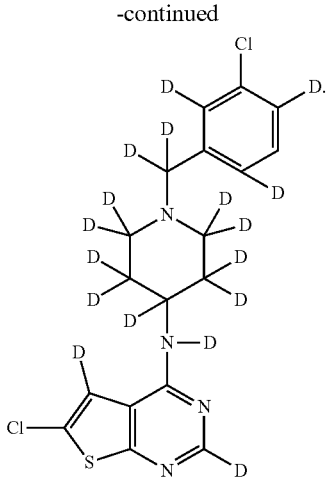
20. The method of claim 19 wherein the compound is selected from the group consisting of
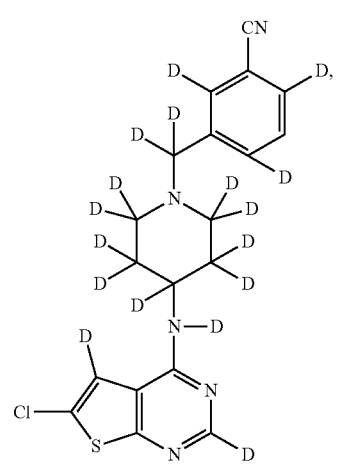
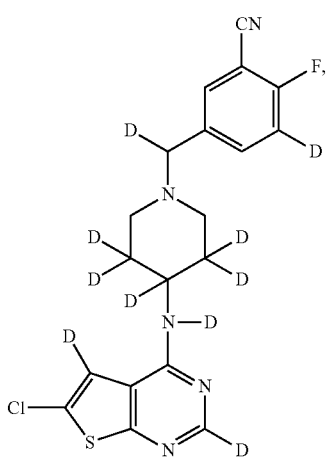
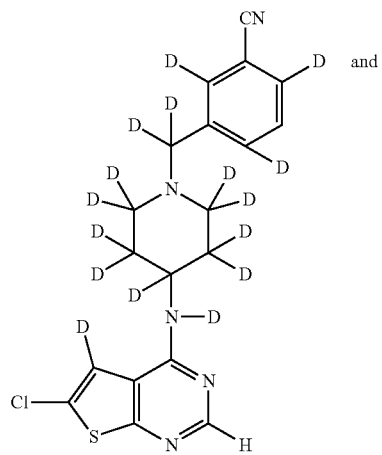
and
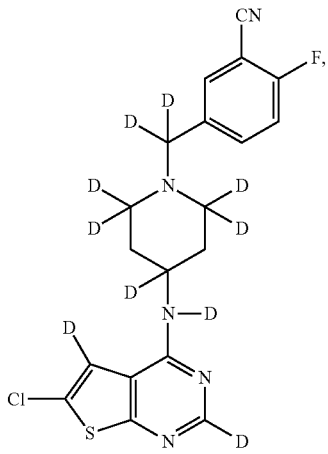

85
-continued
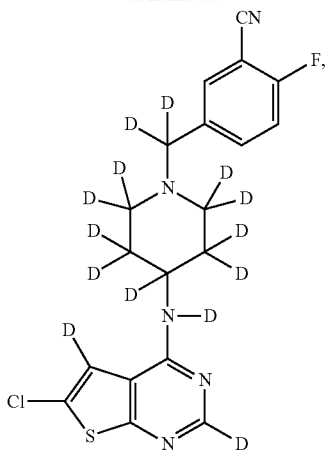
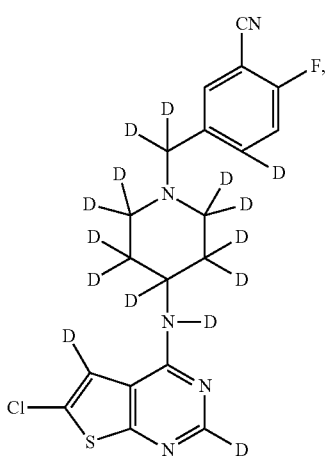
86
-continued
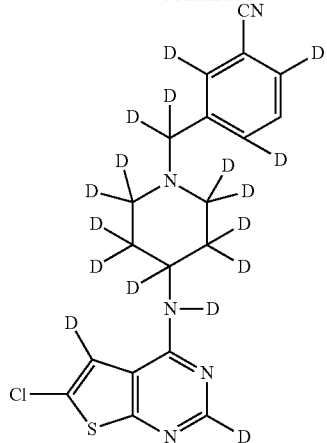
and
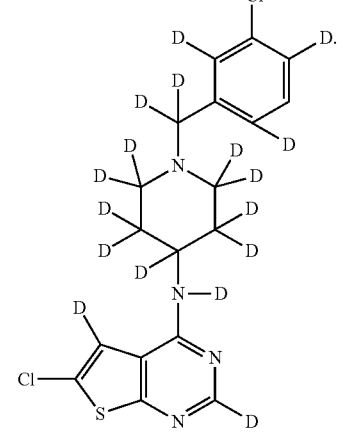
* * * * *